United States Patent
Mathonneau et al.

(10) Patent No.: US 10,993,891 B2
(45) Date of Patent: May 4, 2021

(54) SOLID ANHYDROUS COSMETIC COMPOSITION, PREPARATION PROCESS, COSMETIC TREATMENT PROCESSES AND ASSOCIATED KIT

(71) Applicant: L'OREAL, Paris (FR)

(72) Inventors: Estelle Mathonneau, Saint Ouen (FR); Gregory Plos, Saint Ouen (FR); Emmanuelle Lebon-Hipolite, Saint Ouen (FR); Marie-Florence D'Arras, Saint Ouen (FR); Rafik Kerboussa, Saint Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/537,071

(22) PCT Filed: Dec. 15, 2015

(86) PCT No.: PCT/EP2015/079702
§ 371 (c)(1),
(2) Date: Jun. 16, 2017

(87) PCT Pub. No.: WO2016/096792
PCT Pub. Date: Jun. 23, 2016

(65) Prior Publication Data
US 2017/0348200 A1 Dec. 7, 2017

(30) Foreign Application Priority Data

Dec. 19, 2014 (FR) ........................................ 1462896
Dec. 19, 2014 (FR) ........................................ 1462911

(51) Int. Cl.
*A61K 8/00* (2006.01)
*A61K 8/02* (2006.01)
*A61K 8/44* (2006.01)
*A61K 8/46* (2006.01)
*A61Q 5/02* (2006.01)
*A61Q 5/12* (2006.01)

(52) U.S. Cl.
CPC ............ *A61K 8/0225* (2013.01); *A61K 8/44* (2013.01); *A61K 8/463* (2013.01); *A61Q 5/02* (2013.01); *A61Q 5/12* (2013.01)

(58) Field of Classification Search
CPC .......... A61K 8/0225; A61K 8/44; A61Q 5/02
See application file for complete search history.

(56) References Cited

U.S. PATENT DOCUMENTS

| 3,472,840 A | 10/1969 | Stone et al. |
| 3,589,978 A | 6/1971 | Kamal et al. |
| 3,910,862 A | 10/1975 | Barabas et al. |
| 4,031,307 A | 6/1977 | DeMartino et al. |
| 4,131,576 A | 12/1978 | Iovine et al. |
| 4,137,180 A | 1/1979 | Naik et al. |
| 4,165,367 A | 8/1979 | Chakrabarti |
| 4,185,087 A | 1/1980 | Morlino |
| 4,223,009 A | 9/1980 | Chakrabarti |
| 4,330,438 A | 5/1982 | Dierassi et al. |
| 4,874,554 A | 10/1989 | Lange et al. |
| 4,957,732 A | 9/1990 | Grollier et al. |
| 6,235,696 B1 | 5/2001 | Hensen et al. |
| 6,235,913 B1 | 5/2001 | Raths et al. |
| 6,300,297 B1 | 10/2001 | Seipel et al. |
| 6,300,508 B1 | 10/2001 | Raths et al. |
| 6,451,297 B1 | 9/2002 | Benoit et al. |
| 2003/0180242 A1* | 9/2003 | Eccard .................... A61K 8/046 424/70.11 |
| 2011/0081392 A1* | 4/2011 | de Arruda ................ A61Q 5/02 424/401 |

FOREIGN PATENT DOCUMENTS

| DE | 19806495 C1 | 1/1999 |
| EP | 0186507 A2 | 7/1986 |
| EP | 0342834 A2 | 11/1989 |
| EP | 0530974 A1 | 3/1993 |
| FR | 1492597 A | 8/1967 |
| FR | 2077143 A5 | 10/1971 |
| FR | 2393573 A1 | 1/1979 |
| JP | S63-135317 A | 6/1988 |
| JP | H05-247495 A | 9/1993 |
| JP | 2002-338994 A | 11/2002 |
| WO | 96/17922 A1 | 6/1996 |
| WO | 2009/153311 A2 | 12/2009 |

OTHER PUBLICATIONS

International Search Report for PCT/EP2015/079702, dated Feb. 12, 2016.
Todd, Charles, et al., "Volatile Silicone Fluids for Cosmetic Formulations," Cosmetics and Toiletries, vol. 91, Jan. 1976, pp. 29-32.
Mintel: "Little Green Bag," XP002741550, Aug. 2011.

* cited by examiner

*Primary Examiner* — Necholus Ogden, Jr.
(74) *Attorney, Agent, or Firm* — The Marbury Law Group, PLLC

(57) ABSTRACT

Solid anhydrous cosmetic composition, preparation process, cosmetic treatment processes and associated kit The present invention relates to a solid anhydrous cosmetic composition, in particle form, and comprising at least 30% by weight of anionic surfactants, at least 5% by weight of amphoteric surfactants, and at least 10% by weight of fillers. The invention also relates to a process for preparing this composition by granulation on a fluidized air bed and also to a process for the cosmetic treatment, in particular the care and/or the cleaning, of keratin materials, in particular the hair, comprising the application of said solid anhydrous cosmetic composition, alone or in combination with a hair conditioning composition. The invention also relates to a kit comprising said solid anhydrous cosmetic composition and said conditioning composition.

15 Claims, No Drawings

SOLID ANHYDROUS COSMETIC COMPOSITION, PREPARATION PROCESS, COSMETIC TREATMENT PROCESSES AND ASSOCIATED KIT

CROSS REFERENCE TO RELATED APPLICATIONS

This is a national stage application of PCT/EP2015/079702, filed internationally on Dec. 15, 2015, which claims priority to French Application Nos. 1462911 and 1462896, both filed on Dec. 19, 2014, which are all incorporated by reference herein in their entireties.

The present invention relates to cosmetic compositions, in particular for cleaning or washing keratin materials, in particular the hair, which are in solid anhydrous form, and also to a process for preparing these compositions.

The present invention also relates to a process for the cosmetic treatment, in particular the cleaning and the conditioning, of the hair, using these solid anhydrous cosmetic compositions, alone or in combination with hair conditioning compositions, and also to the kit comprising said two compositions.

Many cosmetic washing products are known in the hair hygiene field. They are generally intended for cleaning keratin materials while at the same time providing them with good cosmetic properties.

Conventional products for cleaning keratin materials, such as shampoos, are usually in the form of more or less thickened liquids. However, these products can prove to be difficult to meter out; the more liquid they are, the greater their tendency to run through the fingers, making it difficult to meter them out and creating waste, and/or the greater their tendency to leak out of their packaging, which can be very bothersome when they come into contact with clothing, for example during moving.

In order to modify the texture, and in particular to make it more compact, conventional means consist in using thickeners, but this is often done to the detriment of the cosmetic effects of the composition. In addition, it has been noted that thicker compositions often have the drawback of requiring a lot of rinsing water in order to remove the surplus product on the hair. In many countries where access to water is restricted, the rinsing time and therefore the amount required to properly rinse-off the product are key indicators of the use qualities of a composition.

In order to overcome some of these problems, solid cosmetic formulations have been proposed, in particular shampoos in the form of granules or of solid powder.

Mention may particularly be made of U.S. Pat. No. 4,330,438 which describes shampoo concentrates in powder form comprising anionic surfactants and non-ionic derivatives of galactomannan, which form shampoos after dilution with water.

Mention may also be made of EP796318 which describes solid compositions obtained by drying and granulation of surface-active aqueous pastes in the presence of solid fillers, such as wood flours.

Mention may also be made of WO 2009/153311 which describes granulated shampoos comprising at least one surfactant deposited on solid particles. In said document, an aqueous phase comprising the surfactant is brought into contact with a solid phase constituted of fillers, in such a way that the surfactant agglomerates on the fillers. This step can be carried out in a mixer-granulator, in a mixer or in a fluidized bed granulator.

However, the solid compositions thus prepared may disaggregate or disintegrate with difficulty in the presence of water, and do not always make it possible to obtain rapid initiation of foaming and/or a sufficient abundance of foam. They can also be difficult to remove by rinsing, and can leave residues on the hair, which may then impact the cosmetic or aesthetic performance levels of the product.

There is therefore the need to have compositions for washing keratin materials which do not run and which are more compact, modelable and economical. The compositions desired must disaggregate or disintegrate easily, must be easy to apply to keratin materials, and must allow rapid initiation of foaming, i.e. the rapid obtaining of an appropriate and sufficiently abundant foam, when the composition is applied, generally by rubbing, to said keratin materials which have optionally been pre-wetted.

The objective of the present invention is to provide such compositions, which do not have the drawbacks of the prior art, and which are capable of rapidly enabling a foam appropriate for washing keratin materials to be obtained.

A subject of the invention is thus a solid anhydrous cosmetic composition in particle form, comprising:
  at least 30% by weight, relative to the total weight of the composition, of one or more anionic surfactants,
  at least 5% by weight, relative to the total weight of the composition, of one or more amphoteric surfactants,
  at least 10% by weight, relative to the total weight of the composition, of one or more fillers.

Another subject of the invention is a process for preparing said solid anhydrous cosmetic composition, by granulation on a fluidized air bed, in which:
  a liquid phase comprising at least one solvent is sprayed onto a solid phase comprising at least 50% by weight, relative to the total weight of said solid phase, of one or more surfactants chosen from anionic and amphoteric surfactants, and mixtures thereof.

Another subject of the invention is a solid anhydrous cosmetic composition in particle form, which can be obtained by means of said process of granulation on a fluidized air bed.

Another subject of the invention is a process for the cosmetic treatment, in particular the care and/or the cleaning, of keratin materials, in particular the hair, the scalp, bodily skin and/or facial skin, comprising the application, to said keratin materials, of a solid anhydrous cosmetic composition as defined above, optionally followed by rinsing, after an optional leave-on time.

The solid anhydrous composition according to the invention has an entirely unusual texture, which is non-tacky; it is simple to take, to handle and to apply; the composition is easy to grasp and is very easy to meter out and to apply.

It disintegrates easily and rapidly on contact with the skin, and makes it possible to rapidly obtain a foam with good staying power and in abundant amount, which is entirely comparable to the foam obtained with a usual cleaning composition, for example of shampoo type.

The solid anhydrous composition is also easy to rinse off, without leaving residues on the hair, while at the same time giving the keratin materials a natural and clean feel after it has been removed.

The solid anhydrous composition according to the invention can be packaged in single-dose form, which is particularly advantageous for example in the context of travelling or of performing sporting activities or rambling (light baggage, limitation of the risks of the product leaking in bags, reduction in waste).

Moreover, it is common practice to use detergent cosmetic compositions such as shampoos or shower gels, based essentially on surfactants, for washing keratin materials such as the skin and the hair. These compositions are generally applied to the keratin materials, which are preferably wet, and the foam generated by massaging or rubbing with the hands or a toiletry flannel makes it possible, after rinsing with water, to remove the diverse types of soiling initially present on the hair or the skin.

These compositions have mainly a washing action, and secondarily a conditioning action on the keratin fibres, in particular the hair.

There are, moreover, care compositions, for example of conditioner type, which have a more extensive conditioning action but without a washing action.

There is also on the market a category of hybrid products, called "low poo" or "no poo" which make it possible to provide a more marked conditioning than with a usual shampoo, while at the same time having a slight detergent activity making it possible to use them without prior shampooing.

As things stand, the balance between washing/detergent power and treating/conditioning power of these products is imposed by their formulation, i.e. the ingredients that they contain and the amount thereof. If consumers wish to modulate these effects, from one use to another, they will have to have several products which have different levels of detergence and/or conditioning. This is also the case when, within the same family, there are various types of hair: here again it will be necessary to have a suitable product per type of hair, hence a multiplication of the products to be purchased.

It could therefore be desirable to have a means making it possible to modulate the detergence and conditioning actions of a composition, for example according to the expectations of the consumer and/or according to the type of hair of said consumer.

One of the objectives of the invention is to provide such a means, making it possible to obtain a washing action and a conditioning action in a single act, these actions being of levels that can be modulated by the user.

A subject of the present invention is therefore also a process for the cosmetic treatment of keratin materials, in particular the hair, comprising the application to said keratin materials, sequentially or simultaneously:
of a solid anhydrous cosmetic composition as defined above, and
of a conditioning composition comprising one or more conditioning agents, in particular chosen from cationic surfactants, cationic and/or amphoteric polymers, silicones, liquid fatty substances, solid fatty substances, and mixtures thereof.

Another subject of the invention is a kit comprising:
a solid anhydrous cosmetic composition as defined above, and
a conditioning composition comprising one or more conditioning agents, in particular chosen from cationic surfactants, cationic and/or amphoteric polymers, silicones, liquid fatty substances, solid fatty substances, and mixtures thereof.

It has been noted that, with the invention, it is possible to modulate on demand the level of detergence and of conditioning obtained, by adjusting the relative amounts of solid anhydrous composition and of liquid conditioning composition used to prepare the final cosmetic composition.

In the present description, the term "final composition" is intended to mean the composition obtained by mixing said solid anhydrous composition and said conditioning composition, whether this mixing is carried out directly on the keratin materials during application, or else in a container or in the hand before application, for example.

The invention also provides consumers, always demanding compositions which are in new galenical forms and/or are capable of being applied in a new way, and/or which can be prepared directly by said consumers just before application, with a kit and an associated cosmetic treatment process enabling users to themselves prepare their cosmetic composition just before its use and/or during its use.

The preparing or the obtaining of the final composition is easy; in particular, by simply adding the solid composition to the conditioning composition, it is possible to obtain a final composition which, after application to the keratin materials, allows the solid composition to disintegrate and produces a creamy texture which is pleasant to the touch and easy to apply to the head of hair; this final creamy composition distributes well on the hair and also rinses off easily and rapidly.

The foam obtained with the final composition is of good quality: the amount thereof varies according to the relative amount of solid composition in the final mixture, but in any event, the foam has good staying power and is creamy.

After rinsing, the hair is light, clean and soft. The level of detergence and of lightness is better than with the use of a conditioning or care composition alone.

In the present description, the expression "at least one" is equivalent to the expression "one or more" and can substitute for said expression, and the expression "between" is equivalent to the expression "ranging from" and can substitute for said expression, and implies that the limits are included.

Solid Anhydrous Composition

The solid anhydrous composition according to the invention is therefore in solid form, in particular in the form of particles such as granules or granular material, or else powder.

Preferably, the particles according to the invention are small fractionated objects formed from solid particles aggregated together, of variable shapes and sizes. They may be regular or irregular in shape. They may in particular have a spherical shape, a square shape, a rectangular shape, or an elongated shape such as rods.

In particular, the composition according to the invention is in the form of small fractionated objects, which can have varied shapes, generally a regular shape and preferably a spherical shape, even better still a well-calibrated (uniform) spherical shape.

Spherical particles are quite particularly preferred.

The size of the particles can be, in the largest dimension thereof, between 0.01 and 5 mm, preferably between 0.1 and 2.5 mm, and better still between 0.5 and 2 mm.

This solid presentation form allows easier handling of the compositions and also facilitated storage.

The composition according to the invention is anhydrous, i.e. it does not comprise water (0%) or, if it does comprise water, the water content is less than or equal to 5% by weight, in particular less than or equal to 2% by weight, or even less than or equal to 1% by weight, even better still less than or equal to 0.5% by weight, relative to the total weight of the composition.

Anionic Surfactants

The solid anhydrous composition according to the invention therefore comprises one or more anionic surfactants. It is therefore a "detergent or washing" composition.

The term "anionic surfactant" is intended to mean a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

The anionic surfactants may be sulfate, sulfonate and/or carboxylic (or carboxylate) surfactants. Needless to say, a mixture of these surfactants may be used.

It is understood in the present description that:
carboxylate anionic surfactants comprise at least one carboxylic or carboxylate function (—COOH or —COO$^-$) and may optionally also comprise one or more sulfate and/or sulfonate functions;
the sulfonate anionic surfactants comprise at least one sulfonate function (—SO$_3$H or —SO$_3^-$) and may optionally also comprise one or more sulfate functions, but do not comprise any carboxylate functions; and
the sulfate anionic surfactants comprise at least one sulfate function but do not comprise any carboxylate or sulfonate functions.

The carboxylic anionic surfactants that may be used thus comprise at least one carboxylic or carboxylate function (—COOH or —COO$^-$).

They may be chosen from the following compounds: acylglycinates, acyllactylates, acylsarcosinates, acylglutamates; alkyl-D-galactosideuronic acids, alkyl ether carboxylic acids, alkyl($C_6$-$C_{30}$ aryl) ether carboxylic acids, alkylamido ether carboxylic acids; and also the salts of these compounds;
the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group;
these compounds possibly being polyoxyalkylenated, in particular polyoxyethylenated, and then preferably comprising from 1 to 50 ethylene oxide units and better still from 2 to 10 ethylene oxide units.

Use may also be made of the $C_6$-$C_{24}$ alkyl monoesters of polyglycoside-polycarboxylic acids, such as $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo.

The polyoxyalkylenated alkyl (amido) ether carboxylic acids that may be used are preferably chosen from those of formula (1):

$$R_1\text{—}(OC_2H_4)_n\text{—}OCH_2COOA \qquad (1)$$

in which:
R$_1$ represents a linear or branched $C_6$-$C_{24}$ alkyl or alkenyl radical, a ($C_8$-$C_9$)alkylphenyl radical, or a radical R$_2$CONH—CH$_2$—CH$_2$— with R$_2$ denoting a linear or branched $C_9$-$C_{21}$ alkyl or alkenyl radical;
preferably, R$_1$ is a $C_8$-$C_{20}$ and preferably $C_8$-$C_{18}$ alkyl radical, and aryl preferably denotes phenyl,
n is an integer or decimal number (average value) ranging from 2 to 24 and preferably from 2 to 10,
A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenated alkyl(amido) ether carboxylic acids that are particularly preferred are those of formula (1) in which:
R$_1$ denotes a $C_{12}$-$C_{14}$ alkyl, cocoyl, oleyl, nonylphenyl or octylphenyl radical,
A denotes a hydrogen or sodium atom, and
n varies from 2 to 20 and preferably from 2 to 10.

Even more preferentially, use is made of compounds of formula (1) in which R denotes a $C_{12}$ alkyl radical, A denotes a hydrogen or sodium atom and n ranges from 2 to 10.

Preferentially, the carboxylic anionic surfactants are chosen, alone or as a mixture, from:
acylglutamates, in particular of $C_6$-$C_{24}$ or even $C_{12}$-$C_{20}$, such as stearoylglutamates, and in particular disodium stearoylglutamate;
acylsarcosinates, in particular of $C_6$-$C_{24}$ or even $C_{12}$-$C_{20}$, such as palmitoylsarcosinates, and in particular sodium palmitoylsarcosinate;
acyllactylates, in particular of $C_{12}$-$C_{28}$ or even $C_{14}$-$C_{24}$, such as behenoyllactylates, and in particular sodium behenoyllactylate;
$C_6$-$C_{24}$, in particular $C_{12}$-$C_{20}$, acylglycinates;
($C_6$-$C_{24}$)alkyl ether carboxylates, and in particular ($C_{12}$-$C_{20}$)alkyl ether carboxylates;
polyoxyalkylenated ($C_6$-$C_{24}$)alkyl(amido) ether carboxylic acids, in particular those comprising from 2 to 50 ethylene oxide groups;
in particular in the form of alkali metal or alkaline-earth metal, ammonium or amino alcohol salts.

The sulfonate anionic surfactants that may be used comprise at least one sulfonate function (—SO$_3$H or —SO$_3^-$).

They may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds;
the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;
these compounds possibly being polyoxyalkylenated, in particular polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:
$C_6$-$C_{24}$, in particular $C_{12}$-$C_{20}$, alkylsulfosuccinates, in particular laurylsulfosuccinates;
$C_6$-$C_{24}$, in particular $C_{12}$-$C_{20}$, alkyl ether sulfosuccinates;
($C_6$-$C_{24}$)acylisethionates, preferably ($C_{12}$-$C_{18}$)acylisethionates,
in particular in the form of alkali metal or alkaline-earth metal, ammonium or amino alcohol salts.

The sulfate anionic surfactants that may be used comprise at least one sulfate function (—OSO$_3$H or —OSO$_3^-$).

They may be chosen from the following compounds: alkyl sulfates, alkyl ether sulfates, alkylamido ether sulfates, alkylaryl polyether sulfates, monoglyceride sulfates; and also the salts of these compounds;
the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, in particular polyoxyethylenated, and then preferably comprising from 1 to 50 ethylene oxide units and better still from 2 to 10 ethylene oxide units.

Preferentially, the sulfate anionic surfactants are chosen, alone or as a mixture, from:

$C_6$-$C_{24}$, or even $C_{12}$-$C_{20}$, alkyl sulfates;
alkyl ether sulfates, in particular of $C_6$-$C_{24}$ or even $C_{12}$-$C_{20}$, preferably comprising from 2 to 20 ethylene oxide units;
in particular in the form of alkali metal or alkaline-earth metal, ammonium or amino alcohol salts.

When the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:

$C_6$-$C_{24}$, in particular $C_{12}$-$C_{20}$, alkyl sulfates;
$C_6$-$C_{24}$ and in particular $C_{12}$-$C_{20}$ alkyl ether sulfates; preferably comprising from 2 to 20 ethylene oxide units;
$C_6$-$C_{24}$, in particular $C_{12}$-$C_{20}$, alkylsulfosuccinates, in particular laurylsulfosuccinates;
$C_6$-$C_{24}$, in particular $C_{12}$-$C_{20}$, alkyl ether sulfosuccinates;
($C_6$-$C_{24}$)acylisethionates, preferably ($C_{12}$-$C_{18}$)acylisethionates;
$C_6$-$C_{24}$, in particular $C_{12}$-$C_{20}$, acylsarcosinates, in particular palmitoylsarcosinates;
($C_6$-$C_{24}$)alkyl ether carboxylates, preferably ($C_{12}$-$C_{20}$) alkyl ether carboxylates;
polyoxyalkylenated ($C_6$-$C_{24}$)alkyl(amido) ether carboxylic acids and salts thereof, in particular those comprising from 2 to 50 alkylene oxide and in particular ethylene oxide groups;
$C_6$-$C_{24}$, in particular $C_{12}$-$C_{20}$, acylglutamates;
$C_6$-$C_{24}$, in particular $C_{12}$-$C_{20}$, acylglycinates;
in particular in the form of alkali metal or alkaline-earth metal, ammonium or amino alcohol salts.

Said anionic surfactant(s) is (are) present in the solid anhydrous composition according to the invention in an amount greater than or equal to 30% by weight, relative to the total weight of the composition, in particular ranging from 30% to 90% by weight, better still from 35% to 75% by weight, even better still from 40% to 60% by weight.

Amphoteric Surfactants

The solid anhydrous composition according to the invention also comprises one or more amphoteric surfactants.

The amphoteric surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, sulfobetaines, ($C_8$-$C_{20}$)alkylsulfobetaines, ($C_8$-$C_{20}$)alkylamido($C_1$-$C_6$)alkylbetaines, such as cocamidopropylbetaine, ($C_8$-$C_{20}$)alkylamido($C_1$-$C_6$)alkylsulfobetaines, and mixtures thereof.

Among the optionally quaternized secondary or tertiary aliphatic amine derivatives that may be used, mention may also be made of the products having the following respective structures (A1) and (A2):

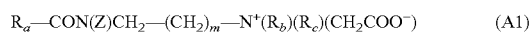

in which:
$R_a$ represents a $C_{10}$-$C_{30}$ alkyl or alkenyl group derived from an acid $R_a$—COOH preferably present in hydrolysed coconut oil, or a heptyl, nonyl or undecyl group,
$R_b$ represents a β-hydroxyethyl group,
$R_c$ represents a carboxymethyl group;
m is equal to 0, 1 or 2,
Z represents a hydrogen atom or a hydroxyethyl or carboxymethyl group,

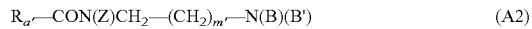

in which:
B represents —$CH_2CH_2OX'$, with X' representing —$CH_2$—COOH, $CH_2$—COOZ', —$CH_2CH_2$—COOH, —$CH_2CH_2$—COOZ', or a hydrogen atom,
B' represents —$(CH_2)_z$—Y', with z=1 or 2, and Y' representing —COOH, —COOZ', —$CH_2$—CHOH—$SO_3H$ or —$CH_2$—CHOH—$SO_3Z'$,
m' is equal to 0, 1 or 2,
Z represents a hydrogen atom or a hydroxyethyl or carboxymethyl group,
Z' represents an ion resulting from an alkali metal or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane,
Ra' represents a $C_{10}$-$C_{30}$ alkyl or alkenyl group of an acid $R_{a'}$ COOH preferably present in hydrolysed linseed oil or coconut oil, an alkyl group, in particular a $C_{17}$ alkyl group, and its iso form, or an unsaturated $C_{17}$ group.

The compounds corresponding to formula (A2) are particularly preferred.

Among the compounds of formula (A2) for which X' represents a hydrogen atom, mention may be made of the compounds known under the (CTFA) names sodium cocoamphoacetate, sodium lauroamphoacetate, sodium caproamphoacetate and sodium capryloamphoacetate.

Other compounds of formula (A2) are known under the (CTFA) names disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

As examples of compounds of formula (A2), mention may be made of the cocoamphodiacetate sold by the company Rhodia under the trade name Miranol® C2M Concentrate, the sodium cocoamphoacetate sold under the trade name Miranol Ultra C 32 and the product sold by the company Chimex under the trade name Chimexane HA.

Use may also be made of compounds of formula (A3):

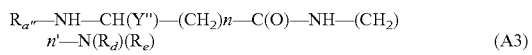

(A3)

in which:
- $R_{a''}$ represents a $C_{10}$-$C_{30}$ alkyl or alkenyl group derived from an acid $R_{a''}$—C(O)OH, which is preferably present in hydrolysed linseed oil or coconut oil;
- Y" represents the group —C(O)OH, —C(O)OZ", —CH$_2$—CH(OH)—SO$_3$H or the group —CH$_2$—CH(OH)—SO$_3$—Z", with Z" representing a cation resulting from an alkali metal or alkaline-earth metal, such as sodium, an ammonium ion or an ion resulting from an organic amine;
- $R_d$ and $R_e$ represent, independently of one another, a $C_1$-$C_4$ alkyl or hydroxyalkyl radical; and
- n and n' denote, independently of one another, an integer ranging from 1 to 3.

Among the compounds of formula (A3), mention may in particular be made of the compound classified in the CTFA dictionary under the name sodium diethylaminopropyl cocoaspartamide and in particular the product sold by the company Chimex under the name Chimexane HB.

Preferably, the amphoteric surfactants are chosen from ($C_8$-$C_{20}$)alkylbetaines, ($C_8$-$C_{20}$)alkylamido($C_1$-$C_6$)alkylbetaines, ($C_8$-$C_{20}$)alkylamphoacetates and ($C_8$-$C_{20}$)alkylamphodiacetates, and mixtures thereof.

Said amphoteric surfactant(s) is (are) present in the solid anhydrous composition according to the invention in an amount greater than or equal to 5% by weight, relative to the total weight of the composition, in particular ranging from 5% to 50% by weight, better still from 7% to 30% by weight, even better still from 10% to 20% by weight.

Fillers

The solid anhydrous composition according to the invention also comprises one or more fillers.

For the purposes of the present invention, the term "filler" is intended to mean mineral or organic, polymeric or non-polymeric solid particles which have no direct cosmetic action on keratin materials.

The fillers according to the invention participate in the solubilization or the disintegration of the solid composition of the invention, in particular in the presence of water.

The mineral fillers can be chosen from solid salts of alkali metals or alkaline-earth metals, in particular sodium or calcium salts, in particular sodium or calcium halides such as sodium chloride and calcium chloride, or else carbonates, in particular sodium or calcium carbonates, for instance calcium carbonate and sodium bicarbonate; mention may also be made of silicate, such as, for example, clays.

The non-polymeric organic fillers can be chosen from monosaccharides, for instance trehalose and sorbitol.

The polymeric organic fillers can be chosen from polysaccharides. Mention may in particular be made of cyclodextrins, starches, alginates, gellans, guar gums, celluloses and wood flours. Among the polymeric organic fillers, mention may also be made of crosslinked polyvinylpyrrolidones and polyacrylates (for example Aquakeep).

Preferably, the fillers according to the invention are chosen from solid salts of alkali metals or alkaline-earth metals, in particular sodium or calcium salts, in particular sodium or calcium halides, such as sodium chloride and calcium chloride, cyclodextrins, starches, clays, and mixtures thereof.

The fillers are present in the solid anhydrous composition according to the invention in an amount greater than or equal to 10% by weight, relative to the total weight of the composition, in particular ranging from 10% to 50% by weight, better still from 12% to 40% by weight, even better still from 15% to 30% by weight.

Amphoteric or Cationic Polymers

The solid anhydrous composition according to the invention can also comprise one or more polymers chosen from amphoteric or cationic polymers, and also mixtures thereof.

The term "cationic polymer" is intended to mean any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5\times10^6$ approximately and preferably between $10^3$ and $3\times10^6$ approximately.

Among the cationic polymers, mention may be made more particularly of:

(1) Homopolymers or copolymers derived from acrylic or methacrylic esters or amides and comprising at least one of the units of the following formulae:

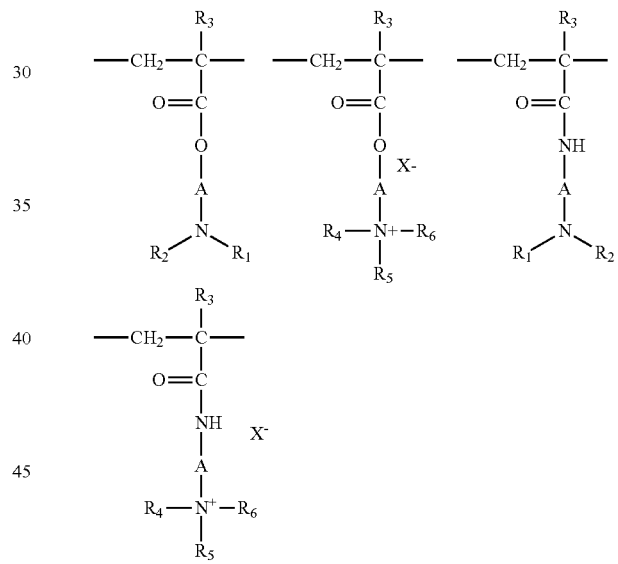

in which:
- $R_3$, which may be identical or different, denote a hydrogen atom or a $CH_3$ radical;
- A, which may be identical or different, represent a linear or branched divalent alkyl group of 1 to 6 carbon atoms, preferably 2 or 3 carbon atoms, or a hydroxyalkyl group of 1 to 4 carbon atoms;
- $R_4$, $R_5$ and $R_6$, which may be identical or different, represent an alkyl group containing from 1 to 18 carbon atoms or a benzyl radical, preferably an alkyl group containing from 1 to 6 carbon atoms;
- $R_1$ and $R_2$, which may be identical or different, represent a hydrogen atom or an alkyl group containing from 1 to 6 carbon atoms, preferably methyl or ethyl;
- X denotes an anion derived from an inorganic or organic acid, such as a methosulfate anion or a halide such as chloride or bromide.

The copolymers of family (1) may also contain one or more units derived from comonomers that may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Among these copolymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, copolymers of acrylamide and of methacryloyloxyethyltrimethylammonium chloride, such as those sold under the name Bina Quat P 100 by the company Ciba Geigy, the copolymer of acrylamide and of methacryloyloxyethyltrimethylammonium methosulfate, such as the product sold under the name Reten by the company Hercules, quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers, such as those sold under the name Styleze CC 10 by ISP, quaternized vinylpyrrolidone/dimethylaminopropylmethacrylamide copolymers such as the product sold under the name Gafquat HS 100 by the company ISP, preferably crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by the company Ciba.

(2) Cationic polysaccharides, in particular cationic celluloses and cationic galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR patent 1 492 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described in particular in U.S. Pat. No. 4,131,576, and mention may be made of hydroxyalkyl celluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, a chloride). Such products are in particular sold under the names Jaguar C13 S, Jaguar C 15, Jaguar C 17 and Jaguar C162 by the company Rhodia.

(3) Polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers.

(4) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized.

(5) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyaminoamide preferably of between 0.5:1 and 1.8:1. Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) Cyclopolymers of alkyldiallylamine or of dialkyldiallylammonium, such as the homopolymers or copolymers containing, as main constituent of the chain, units corresponding to formula (I) or (II):

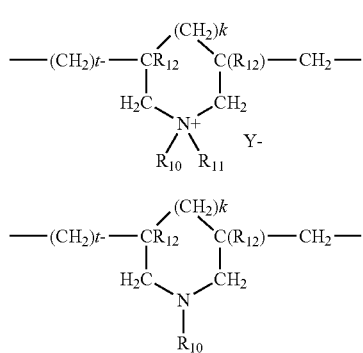

in which k and t are equal to 0 or 1, the sum k+t being equal to 1; $R_{12}$ denotes a hydrogen atom or a methyl radical;

$R_{10}$ and $R_{11}$, independently of one another, denote an alkyl group containing from 1 to 6 carbon atoms, a hydroxyalkyl group in which the alkyl group contains 1 to 5 carbon atoms, a $C_1$-$C_4$ amidoalkyl group; or alternatively $R_{10}$ and $R_{11}$ may denote, together with the nitrogen atom to which they are attached, heterocyclic groups such as piperidinyl or morpholinyl; $R_{10}$ and $R_{11}$, independently of one another, preferably denote an alkyl group containing from 1 to 4 carbon atoms;

$Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer for example sold under the name Merquat 100 by the company Nalco (and homologues thereof of low weight-average molar masses) and the copolymers of diallyldimethylammonium salts (for example chloride) and of acrylamide, sold in particular under the name Merquat 550 or Merquat 7SPR.

(8) Quaternary diammonium polymers comprising repeating units of formula:

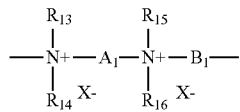

in which:

$R_{13}$, $R_{14}$, $R_{15}$ and $R_{16}$, which may be identical or different, represent aliphatic, alicyclic or arylaliphatic radicals comprising from 1 to 20 carbon atoms, or lower hydroxyalkylaliphatic radicals, or else $R_{13}$, $R_{14}$, $R_{15}$ and $R_{16}$, together or separately, constitute, with the nitrogen atoms to which they are attached, heterocycles optionally comprising a second heteroatom other than the nitrogen, or else $R_{13}$, $R_{14}$, $R_{15}$ and $R_{16}$ represent a linear or branched $C_1$-$C_6$ alkyl radical which is substituted with a nitrile, ester, acyl, amide or —CO—O—$R_{17}$-D or —CO—NH—$R_{17}$-D group in which $R_{17}$ is an alkylene and D is a quaternary ammonium group;

A1 and B1 represent divalent polymethylene groups comprising from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

it being understood that $A_1$, $R_{13}$ and $R_{15}$ can form, with the two nitrogen atoms to which they are attached, a piperazine ring;

in addition, if $A_1$ denotes a linear or branched, saturated or unsaturated alkylene or hydroxyalkylene radical, $B_1$ may also denote a group $(CH_2)_n$—CO-D-OC—$(CH_2)_n$— in which D denotes:

a) a glycol residue of formula —O—Z—O—, in which Z denotes a linear or branched hydrocarbon-based radical, or a group corresponding to one of the following formulae: —$(CH_2$—$CH_2$—O$)_x$—$CH_2$—$CH_2$— and —[$CH_2$—CH($CH_3$)—O$]_y$$CH_2$—CH($CH_3$)—, where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—;

d) a ureylene group of formula: —NH—CO—NH—.

Preferably, $X^-$ is an anion such as chloride or bromide. These polymers have a number-average molar mass (Mn) generally of between 1000 and 100 000.

Mention may be made more particularly of polymers that are composed of repeating units corresponding to the formula:

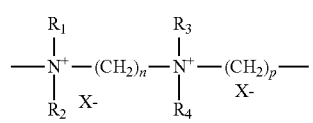

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and $X^-$ is an anion derived from an inorganic or organic acid.

A particularly preferred compound of formula (IV) is that for which $R_1$, $R_2$, $R_3$ and $R_4$ represent a methyl radical and n=3, p=6 and X=Cl, known as Hexadimethrine chloride according to the INCI (CTFA) nomenclature.

(9) Polyquaternary ammonium polymers comprising units of formula (V):

$$-\underset{\underset{R_{19}}{|}}{\overset{\overset{R_{18}}{|}}{N+}}-(CH_2)_r-NH-CO-(CH_2)_q-CO-NH-(CH_2)_s-\underset{\underset{R_{21}}{|}}{\overset{\overset{R_{20}}{|}}{N+}}-A- \quad (V)$$
$$X- \qquad\qquad\qquad\qquad\qquad\qquad\qquad\qquad\qquad X-$$

in which:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2(OCH_2CH_2)_pOH$ radical, in which p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, $X^-$ denotes an anion such as a halide, A denotes a radical of a dihalide or represents preferably —$CH_2$—$CH_2$—O—$CH_2$—$CH_2$—, Examples that may be mentioned include the products Mirapol® A 15, Mirapol® AD1, Mirapol® AZ1 and Mirapol® 175 sold by the company Miranol.

(10) Quaternary polymers of vinylpyrrolidone and of vinylimidazole, for instance the products sold under the names Luviquat® FC 905, FC 550 and FC 370 by the company BASF.

(11) Polyamines such as Polyquart® H sold by Cognis, referred to under the name Polyethylene glycol (15) tallow polyamine in the CTFA dictionary.

(12) Polymers comprising in their structure:

(a) one or more units corresponding to formula (A) below:

$$-CH_2-\underset{\underset{NH_2}{|}}{CH}- \qquad (A)$$

(b) optionally one or more units corresponding to formula (B) below:

$$-CH_2-\underset{\underset{\underset{\underset{O}{\|}}{C-H}}{NH-}}{CH}- \qquad (B)$$

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide. This hydrolysis can be carried out in an acidic or basic medium.

The weight-average molecular weight of said polymer, measured by light scattering, may range from 1000 to 3 000 000 g/mol, preferably from 10 000 to 1 000 000 and more particularly from 100 000 to 500 000 g/mol.

The cationic charge density of these polymers may range from 2 meq/g to 20 meq/g, preferably from 2.5 to 15 meq/g and more particularly from 3.5 to 10 meq/g.

The polymers comprising units of formula (A) and optionally units of formula (B) are sold in particular under the Lupamin name by BASF, such as, for example, in a non-limiting way, the products provided under the names Lupamin 9095, Lupamin 5095, Lupamin 1095, Lupamin 9030 (or Luviquat 9030) and Lupamin 9010.

Preferably, the cationic polymers are chosen from those of families (1), (2), (7) and (10) mentioned above.

Among the cationic polymers mentioned above, the ones that may preferably be used are cationic polysaccharides, in particular cationic celluloses and cationic galactomannan gums, and in particular quaternary cellulose ether derivatives such as the products sold under the name JR 400 by the company Amerchol, cationic cyclopolymers, in particular dimethyldiallylammonium salt (for example chloride) homopolymers or copolymers, sold under the names Merquat 100, Merquat 550 and Merquat S by the company Nalco, and homologues thereof of low weight-average molecular weights, quaternary polymers of vinylpyrrolidone and of vinylimidazole, optionally crosslinked homopolymers or copolymers of methacryloyloxy($C_1$-$C_4$)alkyltri($C_1$-$C_4$)alkylammonium salts, and mixtures thereof.

It is also possible to use amphoteric polymers, which may preferably be chosen from amphoteric polymers comprising the repetition of:

(i) one or more units derived from a monomer of (meth)acrylamide type, (ii) one or more units derived from a monomer of (meth)acrylamidoalkyltrialkylammonium type, and (iii) one or more units derived from an acidic monomer of (meth)acrylic acid type.

Preferably, the units derived from a monomer of (meth)acrylamide type (i) are units of structure (Ia) below:

$$\left[-CH_2-\underset{\underset{\underset{\underset{R_2}{}}{O^{\nearrow}}}{|}}{\overset{\overset{R_1}{|}}{C}}-\right] \qquad (Ia)$$

in which $R_1$ denotes H or $CH_3$ and $R_2$ is chosen from an amino, dimethylamino, tert-butylamino, dodecylamino or —NH—$CH_2OH$ radical.

Preferably, said amphoteric polymer comprises the repetition of only one unit of formula (Ia).

The unit derived from a monomer of (meth)acrylamide type of formula (I) in which $R_1$ denotes H and $R_2$ is an amino radical ($NH_2$) is particularly preferred. It corresponds to the acrylamide monomer per se.

Preferably, the units derived from a monomer of (meth)acrylamidoalkyltrialkylammonium type (ii) are units of structure (IIa) below:

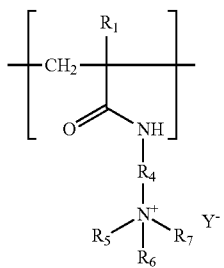

(IIa)

in which:
R$_3$ denotes H or CH$_3$,
R$_4$ denotes a (CH$_2$)$_k$ group with k an integer ranging from 1 to 6 and preferably from 2 to 4;
R$_5$, R$_6$, and R$_7$, which may be identical or different, each denote an alkyl group containing from 1 to 4 carbon atoms;
Y$^-$ is an anion such as bromide, chloride, acetate, borate, citrate, tartrate, bisulfate, bisulfite, sulfate or phosphate.

Preferably, said amphoteric polymer comprises the repetition of only one unit of formula (IIa).

Among these units derived from a monomer of (meth) acrylamidoalkyltrialkylammonium type of formula (IIa), the ones that are preferred are those derived from the methacrylamidopropyltrimethylammonium chloride monomer, for which R$_3$ denotes a methyl radical, k is equal to 3, R$_5$, R$_6$ and R$_7$ denote a methyl radical, and Y$^-$ denotes a chloride anion.

Preferably, the units derived from a monomer of (meth) acrylic acid type (iii) are units of formula (IIIa):

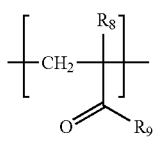

(IIIa)

in which R$_8$ denotes H or CH$_3$ and R$_9$ denotes a hydroxyl radical or an —NH—C(CH$_3$)$_2$—CH$_2$—SO$_3$H radical.

The preferred units of formula (IIIa) correspond to the acrylic acid, methacrylic acid and 2-acrylamino-2-methylpropanesulfonic acid monomers.

Preferably, the unit derived from a monomer of (meth) acrylic acid type of formula (IIIa) is that derived from acrylic acid, for which R$_8$ denotes a hydrogen atom and R$_9$ denotes a hydroxyl radical.

The acidic monomer(s) of (meth)acrylic acid type may be non-neutralized or partially or totally neutralized with an organic or inorganic base.

Preferably, said amphoteric polymer comprises the repetition of only one unit of formula (IIIa).

According to a preferred embodiment of the invention, the amphoteric polymer(s) of this type comprise at least 30 mol % of units derived from a monomer of (meth)acrylamide type (i). Preferably, they comprise from 30 mol % to 70 mol % and more preferably from 40 mol % to 60 mol % of units derived from a monomer of (meth)acrylamide type.

The content of units derived from a monomer of (meth) acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 1 mol % to 20 mol % and preferentially from 5 mol % to 15 mol %.

According to a particularly preferred embodiment of the invention, the amphoteric polymer of this type comprises:
from 30 mol % to 70 mol % and more preferably from 40 mol % to 60 mol % of units derived from a monomer of (meth)acrylamide type (i),
from 10 mol % to 60 mol % and preferentially from 20 mol % to 55 mol % of units derived from a monomer of (meth)acrylamidoalkyltrialkylammonium type (ii), and
from 1 mol % to 20 mol % and preferentially from 5 mol % to 15 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, said amphoteric polymers are constituted solely of units derived from monomers of (meth)acrylamide type (i), of (meth)acrylamidoalkyltrialkylammonium type (ii) and of (meth)acrylic acid type (iii).

Mention may be made, as examples of amphoteric polymers which are particularly preferred, of acrylamide/methacrylamidopropyltrimethylammonium chloride/acrylic acid terpolymers. Such polymers are listed in the CTFA International Cosmetic Ingredient Dictionary, 10th edition 2004, under the name Polyquaternium 53. Corresponding products are in particular sold under the names Merquat 2003 and Merquat 2003 PR by the company Nalco.

As another type of amphoteric polymer that may be used, mention may also be made of copolymers based on (meth) acrylic acid and on a dialkyldiallylammonium salt, and optionally on acrylamide or one of its derivatives, such as copolymers of (meth)acrylic acid and of dimethyldiallylammonium chloride. An example that may be mentioned is Merquat 280 sold by the company Nalco.

The solid anhydrous composition according to the invention may comprise said cationic and/or amphoteric polymers in an amount of between 0.01% and 10% by weight, in particular ranging from 0.1% to 5% by weight and preferentially from 0.2% to 3% by weight, relative to the total weight of the composition.

Silicones

The solid anhydrous cosmetic composition according to the invention may also comprise one or more silicones, which may be solid or liquid, volatile or non-volatile, and amino or non-amino.

The silicones that may be used may be soluble or insoluble in the composition according to the invention; they may be in the form of oil, wax, resin or gum; non-volatile amino silicone or non-amino silicone oils are preferred.

Among the silicones that can be used, mention may be made, alone or as a mixture, of polydialkylsiloxanes and especially polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes comprising in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, in particular polydiphenylsiloxanes, and polyalkylarylsiloxanes functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of polyorganosiloxanes comprising:

polyethyleneoxy and/or polypropyleneoxy groups optionally comprising $C_6$-$C_{24}$ alkyl groups, such as dimethicone copolyols and especially those sold by the company Dow Corning under the name DC 1248 or the oils Silwet® L 722, L 7500, L 77 and L 711 by the company Union Carbide; or ($C_{12}$)alkylmethicone copolyols and especially those sold by the company Dow Corning under the name Q2 5200;

substituted or unsubstituted amine groups, in particular $C_1$-$C_4$ aminoalkyl groups; mention may be made of the products sold under the names GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in U.S. Pat. No. 4,957,732;

anionic groups of the carboxylic acid type, as described, for example, in EP 186 507, or of the alkylcarboxylic type, such as the product X-22-3701E from the company Shin-Etsu; or else of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, such as, for example, the oil 70 047 V 500 000;

the oils of the Mirasil® series sold by the company Rhodia;

the oils of the 200 series from the company Dow Corning, such as DC200 with a viscosity of 60 000 mm²/s;

the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

Products that can be used more particularly in accordance with the invention are mixtures such as:

the mixtures formed from a hydroxy-terminated polydimethylsiloxane or dimethiconol (CTFA), and from a cyclic polydimethylsiloxane, also known as cyclomethicone (CTFA), such as the product Q2-1401 sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ m²/s at 25° C.

Among these polyalkylarylsiloxanes, examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Preferably, the composition according to the invention comprises one or more amino silicones. The term "amino silicone" denotes any silicone comprising at least one primary, secondary or tertiary amine or a quaternary ammonium group.

The weight-average molecular weights of these amino silicones may be measured by gel permeation chromatography (GPC) at ambient temperature (25° C.), as polystyrene equivalents. The columns used are μ styragel columns. The eluent is THF and the flow rate is 1 ml/min. 200 μl of a 0.5% by weight solution of silicone in THF are injected. Detection is performed by refractometry and UV-metry.

As amino silicone that may be used in the context of the invention, mention may be made of:

a) the polysiloxanes corresponding to formula (A):

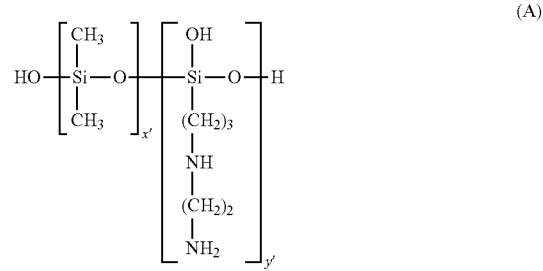

in which x' and y' are integers such that the weight-average molecular weight (Mw) is between 5000 and 500 000 approximately;

b) the amino silicones corresponding to formula (B):

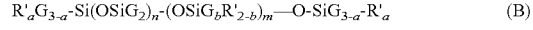

in which:

G, which may be identical or different, denotes a hydrogen atom or a phenyl, OH or $C_1$-$C_8$ alkyl group, for example methyl, or a $C_1$-$C_8$ alkoxy, for example methoxy, a, which may be identical or different, denotes 0 or an integer from 1 to 3, in particular 0, b denotes 0 or 1, in particular 1, m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;

R', which may be identical or different, denotes a monovalent radical of formula —$C_qH_{2q}L$ in which q is a number ranging from 2 to 8 and L is an optionally quaternized amino group chosen from the following groups:

—$N(R'')_2$; —$N^+(R'')_3A^-$; —$NR''-Q-N(R'')_2$ and —$NR''-Q-N^+(R'')_3A^-$, in which R'', which may be identical or different, denotes hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A– represents a cosmetically acceptable anion, especially a halide such as fluoride, chloride, bromide or iodide.

A first group of amino silicones corresponding to formula (B) is represented by the silicones known as "trimethylsilyl amodimethicone", corresponding to formula (C):

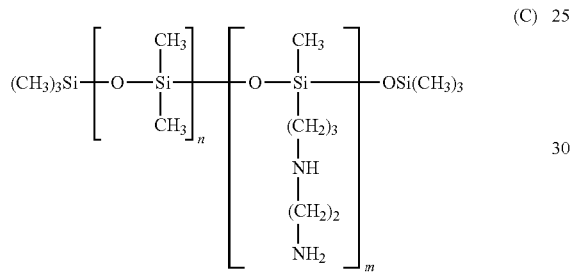

in which m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10.

A second group of amino silicones corresponding to formula (B) is represented by the silicones of formula (D) below:

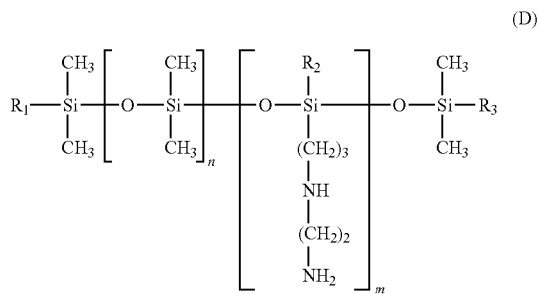

in which:

m and n are numbers such that the sum (n+m) ranges from 1 to 1000 and in particular from 50 to 250 and more particularly from 100 to 200; it being possible for n to denote a number from 0 to 999 and in particular from 49 to 249 and more particularly from 125 to 175, and for m to denote a number from 1 to 1000 and in particular from 1 to 10, and more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of these silicones preferably ranges from 2000 to 1 000 000 and more particularly from 3500 to 200 000.

A third group of amino silicones corresponding to formula (B) is represented by the silicones of formula (E) below:

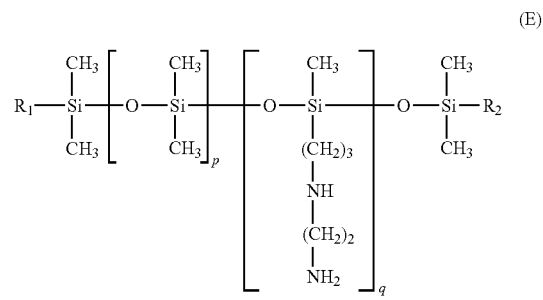

in which:

p and q are numbers such that the sum (p+q) ranges from 1 to 1000, in particular from 50 to 350 and more particularly from 150 to 250; it being possible for p to denote a number from 0 to 999 and especially from 49 to 349 and more particularly from 159 to 239, and for q to denote a number from 1 to 1000, especially from 1 to 10 and more particularly from 1 to 5;

$R_1$ and $R_2$, which are different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly equals 1:0.95.

The weight-average molecular weight (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones whose structure is different from formula (D) or (E).

A product containing amino silicones of structure (D) is sold by the company Wacker under the name Belsil® ADM 652.

A product containing amino silicones of structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants can be of any nature but are preferably cationic and/or non-ionic. The numerical mean size of the silicone particles in the emulsion generally ranges from 3 nm to 500 nm. Preferably, especially as amino silicones of formula (E), use is made of microemulsions whose mean particle size ranges from 5 nm to 60 nm (limits inclusive) and more particularly from 10 nm to 50 nm (limits inclusive). Thus, use may be made according to the invention of the amino silicone microemulsions of formula (E) sold under the names Finish CT 96 E® or SLM 28020® by the company Wacker.

Another group of amino silicones corresponding to formula (B) is represented by the silicones of formula (F) below:

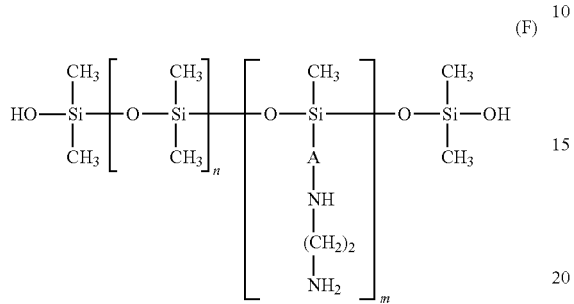

in which:
m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;
A denotes a linear or branched alkylene radical containing from 4 to 8 carbon atoms and preferably 4 carbon atoms. This radical is preferably linear.

The weight-average molecular weight (Mw) of these amino silicones preferably ranges from 2000 to 1 000 000 and even more particularly from 3500 to 200 000.

A silicone corresponding to this formula is, for example, DC2-8299 Cationic Emulsion from Dow Corning.

Another group of amino silicones corresponding to formula (B) is represented by the silicones of formula (G) below:

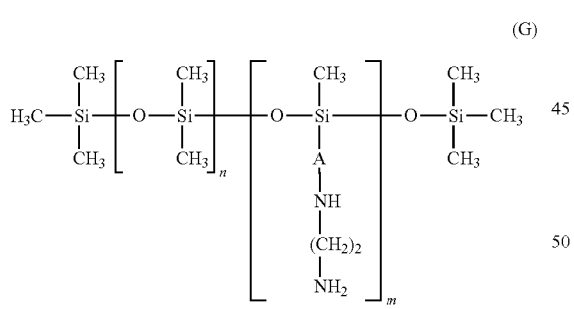

in which:
m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;
A denotes a linear or branched alkylene radical containing from 4 to 8 carbon atoms and preferably 4 carbon atoms. This radical is preferably branched.

The weight-average molecular weight (Mw) of these amino silicones preferably ranges from 500 to 1 000 000 and even more particularly from 1000 to 200 000. A silicone corresponding to this formula is, for example, DC2-8566 Amino Fluid from Dow Corning;

c) the amino silicones corresponding to formula (H):

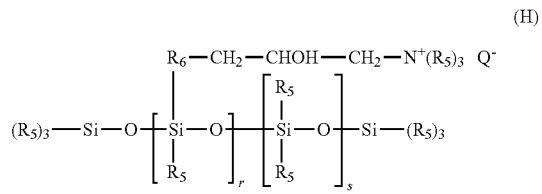

in which:
$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
Q- is an anion such as a halide ion, especially chloride, or an organic acid salt, especially acetate;
r represents a mean statistical value from 2 to 20 and in particular from 2 to 8;
s represents a mean statistical value from 20 to 200 and in particular from 20 to 50.

Such amino silicones are especially described in U.S. Pat. No. 4,185,087;

d) the quaternary ammonium silicones of formula (I):

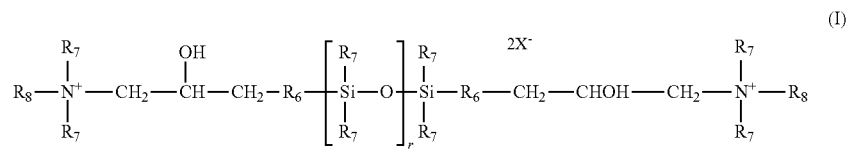

In which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—NHCOR$_7$;
- X— is an anion such as a halide ion, especially chloride, or an organic acid salt, especially acetate;
- r represents a mean statistical value ranging from 2 to 200 and in particular from 5 to 100.

These silicones are described, for example, in Application EP-A-0 530 974;

e) the amino silicones of formula (J):

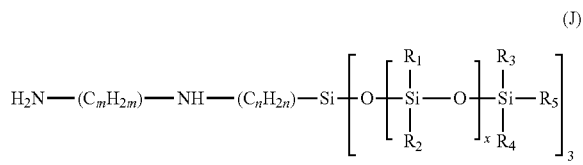

in which:
- $R_1$, $R_2$, $R_3$ and $R_4$, which may be identical or different, denote a $C_1$-$C_4$ alkyl radical or a phenyl group,
- $R_5$ denotes a $C_1$-$C_4$ alkyl radical or a hydroxyl group,
- n is an integer ranging from 1 to 5,
- m is an integer ranging from 1 to 5, and
- x is chosen such that the amine number ranges from 0.01 to 1 meq/g;

f) the multiblock polyoxyalkylenated amino silicones, of the type (AB)n, A being a polysiloxane block and B being a polyoxyalkylene block comprising at least one amine group.

Said silicones preferably are constituted of repeating units of the following general formulae:

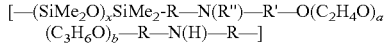

or else

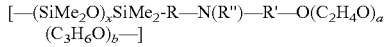

in which:
- a is an integer greater than or equal to 1, preferably ranging from 5 to 200 and more particularly ranging from 10 to 100;
- b is an integer between 0 and 200, preferably ranging from 4 to 100 and more particularly between 5 and 30;
- x is an integer ranging from 1 to 10 000 and more particularly from 10 to 5000;
- R" is a hydrogen atom or a methyl;
- R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —CH2CH2CH2OCH(OH)CH2- radical; preferentially R denotes a —CH2CH2CH2OCH(OH)CH2- radical;
- R', which may be identical or different, represent a linear or branched $C_2$-$C_{12}$ divalent hydrocarbon-based radical, optionally comprising one or more heteroatoms such as oxygen; preferably, R' denotes an ethylene radical, a linear or branched propylene radical, a linear or branched butylene radical, or a —CH2CH2CH2OCH(OH)CH2- radical; preferentially, R denotes —CH(CH3)-CH2-.

The siloxane blocks preferably represent 50 mol % and 95 mol % of the total weight of the silicone, more particularly from 70 mol % to 85 mol %.

The amine content is preferably between 0.02 and 0.5 meq./g of copolymer in a 30% solution in dipropylene glycol, more particularly between 0.05 and 0.2.

The weight-average molecular weight (Mw) of the silicone is preferably between 5000 and 1 000 000 and more particularly between 10 000 and 200 000.

Mention may be made especially of the silicones sold under the names Silsoft A-843 or Silsoft A+ by Momentive.

The solid anhydrous composition according to the invention preferably comprises the silicone(s), and in particular the amino silicone(s), in an amount ranging from 0.01% to 15% by weight, preferably from 0.1% to 10% by weight and preferentially from 0.2% to 5% by weight, relative to the total weight of the composition.

Other Ingredients

The solid anhydrous composition according to the invention may also comprise one or more common cosmetic ingredients, other than the compounds of the invention, chosen especially from plant, mineral, animal or synthetic oils; solid fatty substances and especially waxes, C8-C40 esters and C8-C40 acids; C8-C40 alcohols; cationic surfactants, non-ionic surfactants, anionic polymers; sunscreens; moisturizers; antidandruff agents; antioxidants; chelating agents; nacreous agents and opacifiers; plasticizers or coalescers; hydroxy acids; fragrances; basifying or acidifying agents; aldehydes, DHA; polymeric or non-polymeric thickeners, and in particular associative polymers; preservatives; sequestering agents (EDTA and salts thereof); colorants; soothing agents. Those skilled in the art will take care to choose the ingredients included in the composition, and also the amounts thereof, such that they do not harm the properties of the compositions of the present invention.

Preparation Process

Said solid anhydrous composition can advantageously be prepared by means of a fluidized air bed granulation process, in which:
  a liquid phase comprising at least one solvent is sprayed onto a solid phase comprising at least 50% by weight, relative to the total weight of said solid phase, of one or more surfactants chosen from anionic and amphoteric surfactants, and mixtures thereof.

It is thus possible to obtain a composition which is in the form of particles, in particular as defined above, and quite particularly in the form of spherical particles.

Preferably, the solid phase comprises 50-100% by weight, relative to the weight of said solid phase, of one or more surfactants chosen from anionic and amphoteric surfactants, and mixtures thereof, in particular from 60% to 99% by weight, or even from 80% to 98% by weight.

In one particular embodiment, the solid phase comprises 100% by weight of one or more surfactants chosen from anionic and amphoteric surfactants, and mixtures thereof.

Said anionic and amphoteric surfactants are in particular as defined above.

Preferably, the solid phase comprises 50-100% by weight, relative to said solid phase, in particular 60-99% by weight, of one or more anionic surfactants, in particular as defined above, and even better still chosen from, alone or as a mixture,
- $C_6$-$C_{24}$, in particular $C_{12}$-$C_{20}$, alkyl sulfates;
- $C_6$-$C_{24}$ and in particular $C_{12}$-$C_{20}$ alkyl ether sulfates; preferably comprising from 2 to 20 ethylene oxide units;
- $C_6$-$C_{24}$, in particular $C_{12}$-$C_{20}$, alkylsulfosuccinates, in particular laurylsulfosuccinates;
- $C_6$-$C_{24}$, in particular $C_{12}$-$C_{20}$, alkyl ether sulfosuccinates;
- ($C_6$-$C_{24}$)acylisethionates, preferably ($C_{12}$-$C_{18}$)acylisethionates;
- $C_6$-$C_{24}$, in particular $C_{12}$-$C_{20}$, acylsarcosinates, in particular palmitoylsarcosinates;
- ($C_6$-$C_{24}$)alkyl ether carboxylates, preferably ($C_{12}$-$C_{20}$) alkyl ether carboxylates;
- polyoxyalkylenated ($C_6$-$C_{24}$)alkyl(amido) ether carboxylic acids and salts thereof, in particular those comprising from 2 to 50 alkylene oxide and in particular ethylene oxide groups;
- $C_6$-$C_{24}$, in particular $C_{12}$-$C_{20}$, acylglutamates;
- $C_6$-$C_{24}$, in particular $C_{12}$-$C_{20}$, acylglycinates;

in particular in the form of alkali metal or alkaline-earth metal, ammonium or amino alcohol salts.

Preferably, the solid phase comprises 0-50% by weight, relative to said solid phase, in particular 1 to 35% by weight, of one or more amphoteric surfactants, in particular as defined above, and even better still chosen from, alone or as a mixture, ($C_8$-$C_{20}$)alkylbetaines, ($C_8$-$C_{20}$)alkylamido($C_1$-$C_6$)alkylbetaines, ($C_8$-$C_{20}$)alkyl amphoacetates and ($C_8$-$C_{20}$)alkyl amphodiacetates.

The solid phase may also comprise polymers, for example cationic polymers, in particular as defined above, in pulverulent form, and/or fillers, in particular as defined above.

The solid phase is anhydrous, i.e. it does not comprise water (0%) or, if it does comprise water, the water content is less than or equal to 5% by weight, in particular less than or equal to 2% by weight, or even less than or equal to 1% by weight, even better still less than or equal to 0.5% by weight, relative to the total weight of said phase.

The liquid phase comprises at least one solvent; preferably, this solvent comprises water or a water-$C_1$-$C_4$ mono alcohol mixture; preferably, the liquid phase comprises at least 50% by weight, relative to the weight of said phase, of solvent, in particular at least 50% of water.

Preferably, the liquid phase may comprise one or more surfactants chosen from anionic and amphoteric surfactants.

Preferably, the liquid phase comprises 0-60% by weight, in particular 1-40% by weight, even better still 5-30% by weight, of one or more anionic surfactants, in particular as defined above, and even better still chosen from, alone or as a mixture,
- $C_6$-$C_{24}$, in particular $C_{12}$-$C_{20}$, alkyl sulfates;
- $C_6$-$C_{24}$ and in particular $C_{12}$-$C_{20}$ alkyl ether sulfates; preferably comprising from 2 to 20 ethylene oxide units;
- $C_6$-$C_{24}$, in particular $C_{12}$-$C_{20}$, alkylsulfosuccinates, in particular laurylsulfosuccinates;
- $C_6$-$C_{24}$, in particular $C_{12}$-$C_{20}$, alkyl ether sulfosuccinates;
- ($C_6$-$C_{24}$)acylisethionates, preferably ($C_{12}$-$C_{18}$)acylisethionates;
- $C_6$-$C_{24}$, in particular $C_{12}$-$C_{20}$, acylsarcosinates, in particular palmitoylsarcosinates;
- ($C_6$-$C_{24}$)alkyl ether carboxylates, preferably ($C_{12}$-$C_{20}$) alkyl ether carboxylates;
- polyoxyalkylenated ($C_6$-$C_{24}$)alkyl(amido) ether carboxylic acids and salts thereof, in particular those comprising from 2 to 50 alkylene oxide and in particular ethylene oxide groups;
- $C_6$-$C_{24}$, in particular $C_{12}$-$C_{20}$, acylglutamates;
- $C_6$-$C_{24}$, in particular $C_{12}$-$C_{20}$, acylglycinates;

in particular in the form of alkali metal or alkaline-earth metal, ammonium or amino alcohol salts.

Preferably, the liquid phase may comprise 0-20% by weight, in particular from 1 to 15% by weight, even better still from 2% to 10% by weight, of one or more amphoteric surfactants, in particular as defined above, and even better still chosen from, alone or as a mixture, ($C_8$-$C_{20}$)alkylbetaines, ($C_8$-$C_{20}$)alkylamido($C_1$-$C_6$)alkylbetaines, ($C_8$-$C_{20}$)alkyl amphoacetates and ($C_8$-$C_{20}$)alkyl amphodiacetates.

In one particular embodiment, the liquid phase comprises no amphoteric surfactant and/or no anionic surfactant.

The liquid phase may also comprise one or more fillers as defined above. Preferably, said fillers may be present in a proportion of from 2% to 80% by weight, in particular from 5% to 75% by weight or even from 10% to 50% by weight, of the total weight of the liquid phase.

The liquid phase may also comprise one or more cationic polymers as defined above, and/or one or more silicones as defined above; it may also comprise water-soluble or water-dispersible cosmetic additives, and in particular fragrances, water-soluble cosmetic active agents and colorants.

Preferably, the liquid phase comprises 0-60% by weight, in particular 1-40% by weight, even better still 5-30% by weight, relative to the weight of the final composition, obtained after granulation, of one or more anionic surfactants.

Preferably, the liquid phase comprises 0-100% by weight, in particular 50-100% by weight, even better still 80-95% by weight, relative to the weight of the final composition, obtained after granulation, of one or more amphoteric surfactants.

Preferably, the liquid phase comprises 0-100% by weight, in particular 50-100% by weight, even better still 80-100% by weight, relative to the weight of the final composition, of one or more fillers.

In one particular embodiment, the liquid phase comprises all (100%) of the fillers present in the final composition.

In one particular embodiment, the liquid phase comprises no fillers at all (0%).

Generally, and in a manner known to those skilled in the art, it can be said that the fluidized air bed granulation of the particles is a process which brings into contact three phases: solid, liquid and gas. It is a complex process which combines simultaneous and competing steps such as mixing, spraying, wetting and drying.

The principle is relatively simple: the solid particles are suspended in the bed by a current of hot air and a solution containing the binder is injected therein. The heat required to evaporate the solvent is provided by the fluidization air. This technique has the advantage of carrying out several operations such as wetting, mixing and drying in the same apparatus.

The wet agglomeration of solid particles in a fluidized bed is the result of a succession of elementary steps, namely wetting of the surface of the particles by the liquid (binder), collision and adhesion of particles to one another. These steps all take place in the same apparatus.

The load of particles is placed in motion by an ascending stream of hot air (fluidization air), allowing the individualization and mixing of the particles. The spraying of liquid in the bed makes it possible to wet the surface of the particles which come into contact with the jet, while making said surface tacky.

Depending on the conditions of drying by the hot air, the liquid deposited (drop) will serve, on contact with another particle, to establish a liquid bridge (or link) which will be solidified by drying. Repeating the wetting, collision and drying steps results in the growth by agglomeration (or coalescence) that is desired. Owing to the agitation of the bed, the agglomerates are subjected to impacts, and there is competition between coalescence and rupture.

The objective of the various pieces of equipment used for the agglomeration is to bring the particles into contact with the drops of binder solution, and then to bring the wetted particles into contact with one another.

The operation may be batchwise or continuous, with the possibility of recycling the fines for example.

A preferred embodiment of preparation of the composition according to the invention is described hereinafter, this embodiment being merely an illustration and in no way limiting.

Thus, according to this preferred embodiment: in a fluidized bed, the solid phase (comprising the solid particles) is placed in motion (the particles are individualized) by an ascending stream of hot air (or gas). The spraying of the liquid phase in fine drops (10-50 microns for example) above or within the fluidized bed of particles allows their surface to be wetted. Owing to the considerable agitation, the wet particles collide with one another, allowing the formation of liquid bridges between particles, said bridges being very rapidly solidified by drying (evaporation of the water and/or of the solvent) under the effect of the stream of hot air.

During the particle agglomeration in the fluidized bed, the surface of the particles is wetted by spraying a liquid phase above the bed. A nozzle provides a jet of dispersed liquid which will come into contact with the circulating particles.

Preferably, the atomization pressure is around 500-900 m³/h, in particular 600-800 m³/h.

In a known manner, it has been noted that the spraying pressure can have a direct influence on the size of the droplets of solution sprayed and on the spraying angle. The higher the pressure, the finer the droplets and the narrower the spraying angle. The fine droplets will dry more rapidly on the powder already present in the chamber, thus making it possible to gradually increase the size of the particles of the mixture and to form granules. On the other hand, with a lower pressure, the size of the droplets will increase and said droplets will take longer to dry. In this case, the agglomeration phenomenon will be favoured over that of granulation.

Preferably, in the context of the invention, granulation must be carried out in order to obtain particles which are as spherical as possible, the spraying pressure then being rather high. The hardness can optionally be improved by increasing the number of layers (and therefore the size) without adjusting the spraying pressure, but instead adjusting the spraying time and/or the formula.

The types of atomizers (or nozzles) used can be chosen from:

turbine atomizers: the liquid is introduced at the centre of the rotary disc and follows the path to the edge of the disc driven by centrifugal force, where it is broken up into drops. The jet has an angle of 180° and forms a cloud of drops. The average diameter of the drops produced is in particular from 1 to 600 microns;

(single-fluid) pressure atomizers or single-fluid nozzle atomizers: the jet forms by conversion of the pressure energy into kinetic energy when the liquid passes through the nozzle under pressure (5 to 7 MPa). The liquid enters the atomizer tangentially and exits from the orifice in the form of a jet with an angle which ranges between 40° and 140°. The range of the diameters of drops formed is generally from 10 to 800 microns;

(two-fluid) pneumatic atomizers: they make it possible to obtain various spray modes: hollow cone, full cone or flat jet. The angle of the spray jet ranges between 20° and 60° according to the nozzle configuration. The pressure of the compressed air used is from 0.15 to 0.8 MPa. The dispersion of the liquid in small drops (5 to 300 microns) is provided by the shear forces exerted by the atomization air (or gas) on the liquid phase.

Various phenomena are involved during the agglomeration of solid particles in a fluidized bed: wetting of the surface of the fluidized particles (by the sprayed liquid), collision between the wetted particles, formation of liquid bridges (actual adhesion between sufficiently wetted particles which are tacky at the surface), drying of the liquid bridges, converted into solid bridges (agglomerate consolidation), agglomerate attrition (linked to the mechanical strength and to the agitation of the agglomerates formed).

Preferably, the temperature in the fluidized air bed is between 30 and 60° C., in particular between 35° C. and 45° C. In the process chamber, it is possible to note 3 temperatures: the temperature of the air entering, which is generally about 80-90° C.; the temperature of the product, which is generally about 50-60° C.; and the output temperature, which is generally about 40-50° C.

Use

The solid anhydrous cosmetic composition may be rinsed off or left on after having been applied to the keratin fibres; it is preferably rinsed off, after an optional leave-on time which may be a few minutes.

It especially finds a particularly advantageous application in the field of body and/or hair hygiene, in particular for cleaning the hair and/or the scalp, and also for cleansing and/or removing make up from bodily and/or facial skin. It can thus constitute a shampoo or a shower gel, or else a mask to be rinsed off.

Advantageously, a small amount of solid anhydrous composition according to the invention is taken, and is solubilized/pre-emulsified with water, for example in the hand, so as to form an immediate abundant foam, which is then applied to the keratin materials, and in particular the hair and/or the scalp, before then proceeding in the same way as with a normal liquid shampoo.

It is also possible to apply the solid anhydrous composition directly to the keratin materials, for example the hair, to add a little water for example to the head, and to rub/massage so as to solubilize/pre-emulsify said composition, and thus obtain an immediate abundant foam, before then proceeding in the same way as with a normal liquid shampoo.

It is also possible to wet the keratin materials, for example the hair, and then to apply the composition directly on top, and to exert friction so as to disintegrate the particles and thus obtain an immediate abundant foam, before then proceeding in the same way as with a normal liquid shampoo.

The amount of solid anhydrous composition which can be taken/applied can for example be about 1 to 3 g.

It can be left on, in particular for a few minutes, and then rinsed off, for example with water, so as to remove the foam and the dirt.

A subject of the invention is thus also a process for the cosmetic treatment, in particular the care and/or the cleaning, of keratin materials, in particular the hair, the scalp, bodily skin and/or facial skin, comprising the application, to said keratin materials, of a cosmetic composition according to the invention, optionally followed by rinsing, after an optional leave-on time.

The invention particularly relates to a cosmetic process for cleaning human keratin materials, in which a composition according to the invention is applied to said keratin materials, in the presence of water, massaging is carried out so as to form a foam, then the foam formed and the dirt are removed by rinsing with water, after an optional leave-on time.

Conditioning Composition

The second composition which can be used in one of the cosmetic treatment processes according to the invention is a conditioning composition which comprises one or more conditioning agents.

Preferably, this conditioning composition is in liquid form; it can also be in a thicker form, for example in cream form. Preferably, the viscosity of said composition is such that it is compatible with good disintegration of the solid composition.

Advantageously, this conditioning composition is aqueous, i.e. it comprises water at a concentration of at least 40% by weight, preferably ranging from 50% to 99% by weight, in particular from 60% to 98% by weight and better still from 70% to 95% by weight, relative to the total weight of said composition.

This composition comprises one or more conditioning agents.

As conditioning agent which can be used, mention may in particular be made of:
  cationic surfactants;
  cationic and/or amphoteric polymers;
  silicones;
  liquid fatty substances, and in particular liquid fatty acids, which may be hydroxylated on non-hydroxylated; liquid fatty alcohols; mineral, vegetable or animal oils; liquid fatty esters; liquid hydrocarbons;
  solid fatty substances, and in particular solid fatty alcohols; solid fatty esters; ceramides; animal, vegetable or mineral waxes other than ceramides;
  and mixtures thereof.

i) Cationic Surfactants

The conditioning composition according to the invention can therefore comprise one or more cationic surfactants as conditioning agent.

They are advantageously chosen from optionally polyoxyalkylenated primary, secondary or tertiary fatty amine salts, quaternary ammonium salts, and mixtures thereof.

Mention may in particular be made of:
  the quaternary ammonium salts of formula (Ia):

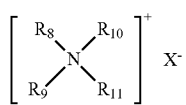
(Ia)

in which:
  the groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ containing from 8 to 30 and preferably from 12 to 24 carbon atoms, it being possible for the aliphatic groups to comprise heteroatoms such as, in particular, oxygen, nitrogen, sulfur and halogens; and
  $X^-$ is an anion in particular chosen from the group of halides, phosphates, acetates, lactates, $(C_1-C_4)$alkylsulfates, $(C_1-C_4)$alkylsulfonates and $(C_1-C_4)$alkylarylsulfonates.

The aliphatic groups are for example chosen from $C_1-C_{30}$ alkyl, $C_1-C_{30}$ alkoxy, $(C_2-C_6)$ polyoxyalkylène, $C_1-C_{30}$ alkylamide, $(C_{12}-C_{22})$alkylamido$(C_2-C_6)$alkyl, $(C_{12}-C_{22})$alkyl acetate, and $C_1-C_{30}$ hydroxyalkyl groups.

Mention may in particular be made of tetraalkylammonium halides, and in particular chlorides, such as dialkyldimethylammonium or alkyltrimethylammonium chlorides in which the alkyl group comprises approximately from 12 to 22 carbon atoms, in particular behenyltriméthylammonium chloride, distearyldimethylammonium chloride, cetyltrimethylammonium chloride and benzyldimethylstearylammonium chloride.

Mention may also be made of palmitylamidopropyltrimethylammonium or stearamidopropyldimethyl-(myristyl acetate)-ammonium halides, and in particular chlorides, in particular the product sold under the name Ceraphyl® 70 by the company Van Dyk;
  the quaternary ammonium salts of imidazoline of formula (Ib):

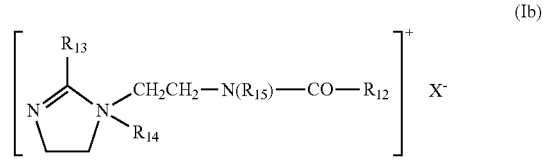
(Ib)

in which
  $R_{12}$ represents an alkenyl or alkyl group comprising from 8 to 30 carbon atoms, for example derived from tallow fatty acids,
  $R_{13}$ represents a hydrogen atom, a $C_1-C_4$ alkyl group or an alkenyl or alkyl group comprising from 8 to 30 carbon atoms,
  $R_{14}$ represents a $C_1-C_4$ alkyl group,
  $R_{15}$ represents a hydrogen atom or a $C_1-C_4$ alkyl group,
  $X^-$ is an anion, for example chosen from the group of halides, phosphates, acetates, lactates, $(C_1-C_4)$alkylsulfates, $(C_1-C_4)$alkylsulfonates and $(C_1-C_4)$alkylarylsulfonates.

Preferably, $R_{12}$ and $R_{13}$ denote a mixture of alkenyl or alkyl groups including from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;
  the di- or triquaternary ammonium salts of formula (IIIb):

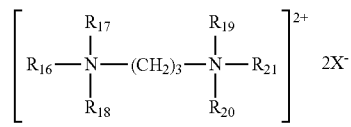
(IIIb)

in which $R_{16}$ denotes an alkyl group comprising approximately from 16 to 30 carbon atoms which is optionally hydroxylated and/or interrupted by one or more oxygen atoms, $R_{17}$ is chosen from hydrogen or an alkyl group comprising from 1 to 4 carbon atoms or a —$(CH_2)_3N^+(R_{16a})(R_{17a})(R_{18a})$ group, in which $R_{16a}$, $R_{17a}$, $R_{18a}$, which may be identical or different, are chosen from hydrogen or an alkyl group comprising from 1 to 4 carbon atoms;

$R_{18}$, $R_{19}$, $R_{20}$ and $R_{21}$, which may be identical or different, are chosen from hydrogen or an alkyl group comprising from 1 to 4 carbon atoms, and $X^-$ is an anion, in particular chosen from the group of halides, acetates, phosphates, nitrates, $(C_1$-$C_4)$alkyl sulfates, $(C_1$-$C_4)$alkyl- or $(C_1$-$C_4)$alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

the quaternary ammonium salts containing one or more ester functions, of formula (IVb) below:

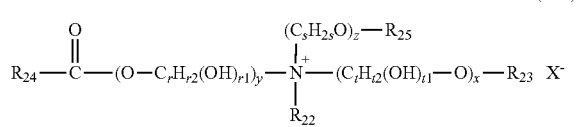

(IVb)

in which:

$R_{22}$ is chosen from $C_1$-$C_6$ alkyl groups and $C_1$-$C_6$ hydroxyalkyl or dihydroxyalkyl groups, $R_{23}$ is chosen from the group $R_{26}$—C(=O)—; linear or branched, saturated or unsaturated $C_1$-$C_{22}$ hydrocarbon-based groups $R_{27}$; and a hydrogen atom, $R_{25}$ is chosen from the group $R_{28}$—C(=O)—; linear or branched, saturated or unsaturated $C_1$-$C_6$ hydrocarbon-based groups $R_{29}$; and a hydrogen atom, $R_{24}$, $R_{26}$ and $R_{28}$, which may be identical or different, are chosen from linear or branched, saturated or unsaturated $C_7$-$C_{21}$ hydrocarbon-based groups, r, s and t, which may be identical or different, are integers having values from 2 to 6, r1 and t1, which may be identical or different, have the values 0 or 1, r2+r1=2 r and t1+t2=2 t, y is an integer ranging from 1 to 10, x and z, which may be identical or different, are integers ranging from 0 to 10, $X^-$ is a simple or complex, organic or inorganic anion, with the proviso that the sum x+y+z is from 1 to 15, that when x=0 then $R_{23}$ denotes $R_{27}$, and that when z=0 then $R_{25}$ denotes $R_{29}$.

The alkyl groups $R_{22}$ may be linear or branched, and more particularly linear. Preferably, $R_{22}$ denotes a methyl, ethyl, hydroxyethyl or dihydroxypropyl group and more particularly a methyl or ethyl group.

Advantageously, the sum x+y+z has a value from 1 to 10.

When $R_{23}$ is an $R_{27}$ hydrocarbon group, it can be long and have from 12 to 22 carbon atoms or be short and have from 1 to 3 carbon atoms.

When $R_{25}$ is an $R_{29}$ hydrocarbon group, it preferably has from 1 to 3 carbon atoms. Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1. Advantageously, y is equal to 1. Preferably, r, s and t, which may be identical or different, are equal to 2 or 3, and even more particularly are equal to 2.

The anion $X^-$ is preferably a halide, preferably chloride, bromide or iodide, a $(C_1$-$C_4)$alkyl sulfate, or a $(C_1$-$C_4)$alkyl- or $(C_1$-$C_4)$alkylarylsulfonate. However, use may be made of methanesulfonate, phosphate, nitrate, tosylate, an anion derived from an organic acid, such as acetate or lactate, or any other anion that is compatible with the ammonium bearing an ester function.

The anion $X^-$ is more particularly still chloride, methyl sulfate or ethyl sulfate.

Use is made more particularly, in the composition according to the invention, of the ammonium salts of formula (IVb) in which:

$R_{22}$ denotes a methyl or ethyl group, x and y are equal to 1, z is equal to 0 or 1, r, s and t are equal to 2, $R_{23}$ is chosen from the group $R_{26}$—C(=O)—, methyl, ethyl or $C_{14}$-$C_{22}$ hydrocarbon-based groups; and a hydrogen atom, $R_{25}$ is chosen from the group $R_{28}$—C(=O)—; and a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (IVb), mention may be made of salts, in particular the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil, such as palm oil or sunflower oil. When the compound comprises several acyl groups, the latter can be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin. Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention can contain, for example, a mixture of quaternary ammonium mono-, di- and triester salts with a predominance by weight of diester salts. It is also possible to use the ammonium salts containing at least one ester function that are described in U.S. Pat. Nos. 4,874,554 and 4,137,180. Use may also be made of behenoylhydroxypropyltrimethylammonium chloride, for example, sold by the company KAO under the name Quartamin BTC 131.

Preferably, the ammonium salts containing at least one ester function comprise two ester functions.

Preferably, when the conditioning composition according to the invention comprises, as beneficial agent, one or more cationic surfactants, they are in particular chosen from those of formula (Ia) or (IVb), better still from the cetyltrimethylammonium, behenyltrimethylammonium and dipalmitoylethylhydroxyethylmethylammonium salts and mixtures thereof; and more particularly from behenyltriméthylammonium chloride, cetyltrimethylammonium chloride, dipalmitoylethylhydroxyethylammonium methosulfate, and mixtures thereof.

Preferably, when the conditioning composition comprises one or more cationic surfactants, it comprises them in an amount ranging from 0.01% to 15% by weight, preferably from 0.1% to 10% by weight and even better still from 0.2% to 6% by weight, relative to the total weight of the composition.

ii) Cationic and Amphoteric Polymers

The conditioning composition according to the invention can comprise, as conditioning agent, one or more polymers chosen from amphoteric or cationic polymers, and also mixtures thereof.

The term "cationic polymer" is intended to mean any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may be made more particularly of:

(1) Homopolymers or copolymers derived from acrylic or methacrylic esters or amides and comprising at least one of the units of the following formulae:

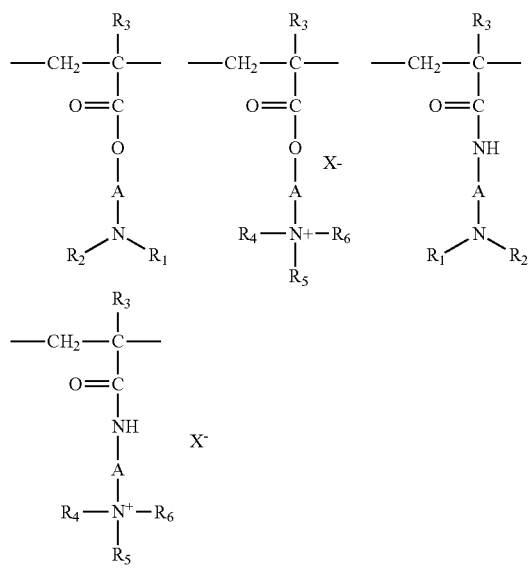

in which:
R$_3$, which may be identical or different, denote a hydrogen atom or a CH$_3$ radical;
A, which may be identical or different, represent a linear or branched divalent alkyl group of 1 to 6 carbon atoms, preferably 2 or 3 carbon atoms, or a hydroxyalkyl group of 1 to 4 carbon atoms;
R$_4$, R$_5$ and R$_6$, which may be identical or different, represent an alkyl group containing from 1 to 18 carbon atoms or a benzyl radical, preferably an alkyl group containing from 1 to 6 carbon atoms;
R$_1$ and R$_2$, which may be identical or different, represent a hydrogen atom or an alkyl group containing from 1 to 6 carbon atoms, preferably methyl or ethyl;
X denotes an anion derived from an inorganic or organic acid, such as a methosulfate anion or a halide such as chloride or bromide.

The copolymers of family (1) may also contain one or more units derived from comonomers that may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Among these copolymers of family (1), mention may be made of:
copolymers of acrylamide and of dimethylaminoethyl methacrylate quaternized with dimethyl sulfate or with a dimethyl halide, such as the product sold under the name Hercofloc by the company Hercules,
copolymers of acrylamide and of methacryloyloxyethyltrimethylammonium chloride, such as those sold under the name Bina Quat P 100 by the company Ciba Geigy,
the copolymer of acrylamide and of methacryloyloxyethyltrimethylammonium methosulfate, such as the product sold under the name Reten by the company Hercules,
quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573,
dimethylaminoethyl methacrylate/vinylcaprolactam/vinylpyrrolidone terpolymers, such as the product sold under the name Gaffix VC 713 by the company ISP,
vinylpyrrolidone/methacrylamidopropyldimethylamine copolymers, such as those sold under the name Styleze CC 10 by ISP,
quaternized vinylpyrrolidone/dimethylaminopropylmethacrylamide copolymers such as the product sold under the name Gafquat HS 100 by the company ISP,
preferably crosslinked polymers of methacryloyloxy(C$_1$-C$_4$)alkyltri(C$_1$-C$_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by the company Ciba.

(2) Cationic polysaccharides, in particular cationic celluloses and cationic galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR patent 1 492 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described in particular in U.S. Pat. No. 4,131,576, and mention may be made of hydroxyalkyl celluloses, for instance hydroxymethyl-, hydroxyethyl- or hydroxypropyl-celluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in U.S. Pat. No. 3,589,578 and 4 031 307, and mention may be made of guar gums comprising cationic trialkylammonium groups. Use is made, for example, of guar gums modified with a 2,3-epoxypropyltrimethylammonium salt (for example, a chloride). Such products are in particular sold under the names Jaguar C13 S, Jaguar C 15, Jaguar C 17 and Jaguar C162 by the company Rhodia.

(3) Polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers.

(4) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized.

(5) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyaminoamide preferably of between 0.5:1 and 1.8:1. Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) Cyclopolymers of alkyldiallylamine or of dialkyldiallylammonium, such as the homopolymers or copolymers containing, as main constituent of the chain, units corresponding to formula (I) or (II):

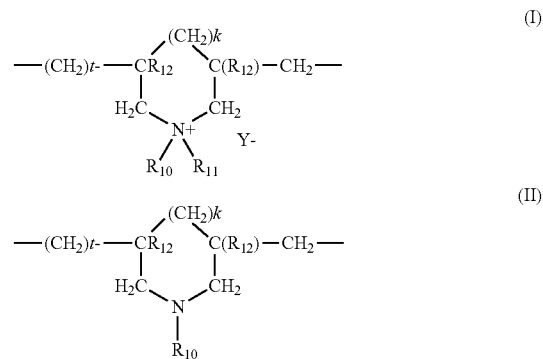

in which k and t are equal to 0 or 1, the sum k+t being equal to 1;

$R_{12}$ denotes a hydrogen atom or a methyl radical;

$R_{10}$ and $R_{11}$, independently of one another, denote an alkyl group containing from 1 to 6 carbon atoms, a hydroxyalkyl group in which the alkyl group contains 1 to 5 carbon atoms, a $C_1$-$C_4$ amidoalkyl group; or alternatively $R_{10}$ and $R_{11}$ may denote, together with the nitrogen atom to which they are attached, heterocyclic groups such as piperidinyl or morpholinyl; $R_{10}$ and $R_{11}$, independently of one another, preferably denote an alkyl group containing from 1 to 4 carbon atoms;

$Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer for example sold under the name Merquat 100 by the company Nalco (and homologues thereof of low weight-average molar masses) and the copolymers of diallyldimethylammonium salts (for example chloride) and of acrylamide, sold in particular under the name Merquat 550 or Merquat 7SPR.

(8) Quaternary diammonium polymers comprising repeating units of formula:

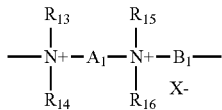 (III)

in which:

$R_{13}$, $R_{14}$, $R_{15}$ and $R_{16}$, which may be identical or different, represent aliphatic, alicyclic or arylaliphatic radicals comprising from 1 to 20 carbon atoms, or lower hydroxyalkylaliphatic radicals, or else $R_{13}$, $R_{14}$, $R_{15}$ and $R_{16}$, together or separately, constitute, with the nitrogen atoms to which they are attached, heterocycles optionally comprising a second heteroatom other than the nitrogen, or else $R_{13}$, $R_{14}$, $R_{15}$ and $R_{16}$ represent a linear or branched $C_1$-$C_6$ alkyl radical which is substituted with a nitrile, ester, acyl, amide or —CO—O—$R_{17}$-D or —CO—NH—$R_{17}$-D group in which $R_{17}$ is an alkylene and D is a quaternary ammonium group;

$A_1$ and $B_1$ represent divalent polymethylene groups comprising from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

it being understood that $A_1$, $R_{13}$ and $R_{15}$ can form, with the two nitrogen atoms to which they are attached, a piperazine ring;

in addition, if $A_1$ denotes a linear or branched, saturated or unsaturated alkylene or hydroxyalkylene radical, $B_1$ may also denote a group $(CH_2)_n$—CO-D-OC—$(CH_2)_n$— in which D denotes:

a) a glycol residue of formula —O—Z—O—, in which Z denotes a linear or branched hydrocarbon-based radical, or a group corresponding to one of the following formulae: —$(CH_2—CH_2—O)_x$—$CH_2$—$CH_2$— and —$[CH_2—CH(CH_3)—O]_y CH_2$—$CH(CH_3)$—, where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—.

d) a ureylene group of formula: —NH—CO—NH—.

Preferably, $X^-$ is an anion such as chloride or bromide. These polymers have a number-average molar mass (Mn) generally of between 1000 and 100 000.

Mention may be made more particularly of polymers that are composed of repeating units corresponding to the formula:

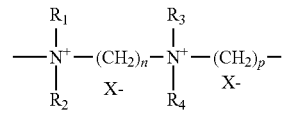 (IV)

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and $X^-$ is an anion derived from an inorganic or organic acid.

A particularly preferred compound of formula (IV) is that for which $R_1$, $R_2$, $R_3$ and $R_4$ represent a methyl radical and n=3, p=6 and X=Cl, known as Hexadimethrine chloride according to the INCI (CTFA) nomenclature.

(9) Polyquaternary ammonium polymers comprising units of formula (V):

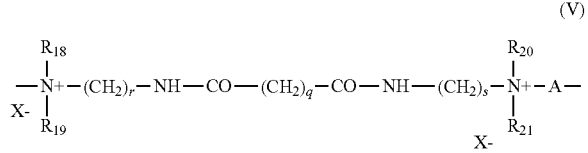 (V)

in which:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2$ $(OCH_2CH_2)_p$OH radical, in which p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X— denotes an anion such as a halide, A denotes a radical of a dihalide or represents preferably —$CH_2$—$CH_2$—O—$CH_2$—$CH_2$—. Examples that may be mentioned include the products Mirapol® A 15, Mirapol® AD1, Mirapol® AZ1 and Mirapol® 175 sold by the company Miranol.

(10) Quaternary polymers of vinylpyrrolidone and of vinylimidazole, for instance the products sold under the names Luviquat® FC 905, FC 550 and FC 370 by the company BASF.

(11) Polyamines such as Polyquart® H sold by Cognis, referred to under the name Polyethylene glycol (15) tallow polyamine in the CTFA dictionary.

(12) Polymers comprising in their structure:

(a) one or more units corresponding to formula (A) below:

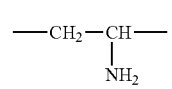 (A)

(b) optionally one or more units corresponding to formula (B) below:

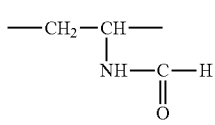

(B)

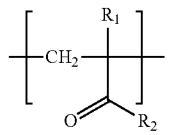

(Ia)

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide. This hydrolysis can be carried out in an acidic or basic medium.

The weight-average molecular weight of said polymer, measured by light scattering, may range from 1000 to 3 000 000 g/mol, preferably from 10 000 to 1 000 000 and more particularly from 100 000 to 500 000 g/mol.

The cationic charge density of these polymers may range from 2 meq/g to 20 meq/g, preferably from 2.5 to 15 meq/g and more particularly from 3.5 to 10 meq/g.

The polymers comprising units of formula (A) and optionally units of formula (B) are sold in particular under the Lupamin name by BASF, such as, for example, in a non-limiting way, the products provided under the names Lupamin 9095, Lupamin 5095, Lupamin 1095, Lupamin 9030 (or Luviquat 9030) and Lupamin 9010.

Preferably, the cationic polymers are chosen from those of families (1), (2), (7) and (10) mentioned above.

Among the cationic polymers mentioned above, the ones that may preferably be used are cationic polysaccharides, in particular cationic celluloses and cationic galactomannan gums, and in particular quaternary cellulose ether derivatives such as the products sold under the name JR 400 by the company Amerchol, cationic cyclopolymers, in particular dimethyldiallylammonium salt (for example chloride) homopolymers or copolymers, sold under the names Merquat 100, Merquat 550 and Merquat S by the company Nalco, and homologues thereof of low weight-average molecular weights, quaternary polymers of vinylpyrrolidone and of vinylimidazole, optionally crosslinked homopolymers or copolymers of methacryloyloxy($C_1$-$C_4$)alkyltri($C_1$-$C_4$)alkylammonium salts, and mixtures thereof.

It is also possible to use amphoteric polymers, which may preferably be chosen from amphoteric polymers comprising the repetition of:

(i) one or more units derived from a monomer of (meth)acrylamide type, (ii) one or more units derived from a monomer of (meth)acrylamidoalkyltrialkylammonium type, and (iii) one or more units derived from an acidic monomer of (meth)acrylic acid type.

Preferably, the units derived from a monomer of (meth)acrylamide type (i) are units of structure (Ia) below:

in which $R_1$ denotes H or $CH_3$ and $R_2$ is chosen from an amino, dimethylamino, tert-butylamino, dodecylamino or —NH—$CH_2$OH radical.

Preferably, said amphoteric polymer comprises the repetition of only one unit of formula (Ia).

The unit derived from a monomer of (meth)acrylamide type of formula (Ia) in which $R_1$ denotes H and $R_2$ is an amino radical ($NH_2$) is particularly preferred. It corresponds to the acrylamide monomer per se.

Preferably, the units derived from a monomer of (meth)acrylamidoalkyltrialkylammonium type (ii) are units of structure (IIa) below:

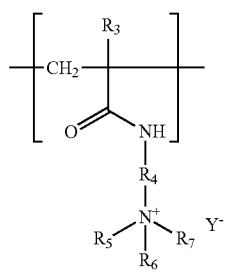

(IIa)

in which:

$R_3$ denotes H or $CH_3$, $R_4$ denotes a $(CH_2)_k$ group with k an integer ranging from 1 to 6 and preferably from 2 to 4;

$R_5$, $R_6$, and $R_7$, which may be identical or different, each denote an alkyl group containing from 1 to 4 carbon atoms;

$Y^-$ is an anion such as bromide, chloride, acetate, borate, citrate, tartrate, bisulfate, bisulfite, sulfate or phosphate.

Preferably, said amphoteric polymer comprises the repetition of only one unit of formula (IIa).

Among these units derived from a monomer of (meth)acrylamidoalkyltrialkylammonium type of formula (IIa), the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the units derived from a monomer of (meth)acrylic acid type (iii) are units of formula (IIIa):

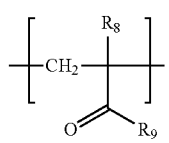

(IIIa)

in which $R_8$ denotes H or $CH_3$ and $R_9$ denotes a hydroxyl radical or an —NH—$C(CH_3)_2$—$CH_2$—$SO_3$H radical.

The preferred units of formula (IIIa) correspond to the acrylic acid, methacrylic acid and 2-acrylamino-2-methylpropanesulfonic acid monomers.

Preferably, the unit derived from a monomer of (meth) acrylic acid type of formula (IIIa) is that derived from acrylic acid, for which $R_8$ denotes a hydrogen atom and $R_9$ denotes a hydroxyl radical.

The acidic monomer(s) of (meth)acrylic acid type may be non-neutralized or partially or totally neutralized with an organic or inorganic base.

Preferably, said amphoteric polymer comprises the repetition of only one unit of formula (IIIa).

According to a preferred embodiment of the invention, the amphoteric polymer(s) of this type comprise at least 30 mol % of units derived from a monomer of (meth)acrylamide type (i). Preferably, they comprise from 30 mol % to 70 mol % and more preferably from 40 mol % to 60 mol % of units derived from a monomer of (meth)acrylamide type.

The content of units derived from a monomer of (meth) acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 1 mol % to 20 mol % and preferentially from 5 mol % to 15 mol %.

According to a particularly preferred embodiment of the invention, the amphoteric polymer of this type comprises:
from 30 mol % to 70 mol % and more preferably from 40 mol % to 60 mol % of units derived from a monomer of (meth)acrylamide type (i),
from 10 mol % to 60 mol % and preferentially from 20 mol % to 55 mol % of units derived from a monomer of (meth)acrylamidoalkyltrialkylammonium type (ii), and
from 1 mol % to 20 mol % and preferentially from 5 mol % to 15 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, said amphoteric polymers are constituted solely of units derived from monomers of (meth)acrylamide type (i), of (meth)acrylamidoalkyltrialkylammonium type (ii) and of (meth)acrylic acid type (iii).

Mention may be made, as examples of amphoteric polymers which are particularly preferred, of acrylamide/methacrylamidopropyltrimethylammonium chloride/acrylic acid terpolymers. Such polymers are listed in the CTFA 10th edition 2004, under the name "Polyquaternium 53". Corresponding products are in particular sold under the names Merquat 2003 and Merquat 2003 PR by the company Nalco.

As another type of amphoteric polymer that may be used, mention may also be made of copolymers based on (meth) acrylic acid and on a dialkyldiallylammonium salt, and optionally on acrylamide or one of its derivatives, such as copolymers of (meth)acrylic acid and of dimethyldiallylammonium chloride. An example that may be mentioned is Merquat 280 sold by the company Nalco.

Preferably, when the conditioning composition according to the invention comprises one or more cationic and/or amphoteric polymers, it comprises them in an amount ranging from 0.01% to 5% by weight, in particular from 0.05% to 3% by weight and preferentially from 0.1% to 2.5% by weight, relative to the total weight of the composition.

iii) Silicones

The conditioning composition according to the invention can comprise one or more silicones as conditioning agent.

The silicones that may be used according to the invention may be soluble or insoluble in the composition; they may be in the form of oils, waxes, resins or gums; they may be volatile or non-volatile.

In particular, the silicones may be organopolysiloxanes, which are in particular insoluble in the composition of the invention. The organopolysiloxanes are in particular described in Walter Noll's "Chemistry and Technology of Silicones" (1968), Academic Press.

The volatile silicones are more particularly chosen from those with a boiling point of between 60° C. and 260° C. Mention may be made of:

i) cyclic volatile silicones comprising from 3 to 7 and preferably 4 to 5 silicon atoms, such as:
octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia;
cyclocopolymers of the dimethylsiloxane/methylalkylsiloxane type having the chemical structure:

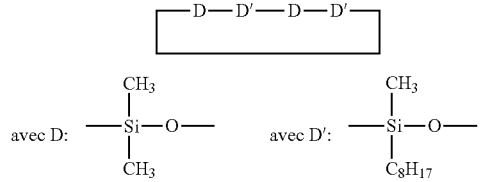

Mention may be made of Volatile Silicone FZ 3109 sold by the company Union Carbide;
mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear volatile silicones containing 2 to 9 silicon atoms, which generally have a viscosity of less than or equal to $5 \times 10^{-6}$ m²/s at 25° C., such as:
decamethyltetrasiloxane; other silicones belonging to this category are described in the article published in Cosmetics and Toiletries, Vol. 91, January 76, pp. 27-32—Todd & Byers *Volatile silicone fluids for cosmetics*; mention may be made of the product sold under the name SH 200 by the company Toray Silicone.

Among the non-volatile silicones, mention may be made of, alone or as a mixture, polydialkylsiloxanes, polydiarylsiloxanes, polyalkylarylsiloxanes, silicone gums and resins, and also organopolysiloxanes which are silicones as defined above, comprising in their structure one or more organofunctional groups attached by means of a hydrocarbon-based group (also called organomodified silicones).

Among the organomodified silicones, mention may be made of polyorganosiloxanes comprising:
polyethyleneoxy and/or polypropyleneoxy groups optionally comprising $C_6$-$C_{24}$ alkyl groups, such as dimethicone copolyols and especially those sold by the company Dow Corning under the name DC 1248 or the oils Silwet® L 722, L 7500, L 77 and L 711 by the company Union Carbide; or ($C_{12}$)alkylmethicone copolyols and especially those sold by the company Dow Corning under the name Q2 5200;

substituted or unsubstituted amine groups, in particular $C_1$-$C_4$ aminoalkyl groups; mention may be made of the products sold under the names GP 4 Silicone Fluid and GP 7100 by the company Genesee, or under the names Q2-8220 and Dow Corning 929 or 939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in U.S. Pat. No. 4,957,732;

anionic groups of the carboxylic acid type, as described, for example, in EP 186 507, or of the alkylcarboxylic type, such as the product X-22-3701E from the company Shin-Etsu; or else of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834; mention may be made, for example, of the product Q2-8413 from the company Dow Corning.

Preferably, when the conditioning composition according to the invention comprises one or more silicones, it comprises them in an amount ranging from 0.01% to 30% by weight, preferably from 0.1% to 10% by weight and even better still from 0.2% to 5% by weight, relative to the total weight of the composition.

iv) Liquid Fatty Substances

The conditioning composition according to the invention may comprise, as conditioning agent, one or more liquid fatty substances, in particular chosen from liquid fatty alcohols, mineral, vegetable or animal oils, liquid fatty esters, liquid hydrocarbons, and mixtures thereof.

The liquid fatty alcohols may be linear or branched; they preferably comprise 8 to 30 carbon atoms; they may be saturated or unsaturated.

The saturated liquid fatty alcohols are preferably branched. They may optionally comprise in their structure at least one aromatic or non-aromatic ring. They are preferably acyclic. More particularly, the saturated liquid fatty alcohols are chosen from octyldodecanol, isostearyl alcohol, 2-hexyldecanol, and also palmityl, myristyl, stearyl and lauryl alcohols, and mixtures thereof.

The unsaturated liquid fatty alcohols contain in their structure at least one double or triple bond, and preferably one or more double bonds. When several double bonds are present, there are preferably 2 or 3 of them, and they may be conjugated or unconjugated. They may optionally comprise in their structure at least one aromatic or non-aromatic ring. They are preferably acyclic. More particularly, the liquid unsaturated fatty alcohols are chosen from oleyl alcohol, linoleyl alcohol, linolenyl alcohol and undecylenyl alcohol, and mixtures thereof.

Among the mineral, vegetable or animal oils that can be used, mention may be made in particular, as oils of plant origin, of sweet almond oil, avocado oil, castor oil, olive oil, jojoba oil, sunflower oil, wheatgerm oil, sesame oil, groundnut oil, grapeseed oil, soybean oil, rapeseed oil, safflower oil, coconut oil, corn oil, hazelnut oil, shea butter oil, palm oil, apricot kernel oil or beauty-leaf oil; as oil of animal origin, perhydrosqualene; as oils of mineral origin, liquid paraffin and liquid petroleum jelly; and mixtures thereof.

The liquid fatty esters may be esters of mono alcohols or of polyols with monoacids or polyacids, at least one of the alcohols and/or acids comprising at least one chain of more than 7 carbon atoms. Preferably, the liquid fatty ester according to the invention is chosen from esters of a fatty acid and of a mono alcohol. Preferably, at least one of the alcohols and/or acids is branched. Mention may be made of isopropyl myristate, isopropyl palmitate, isononyl or isostearyl isononanoate, 2-ethylhexyl palmitate, 2-hexyldecyl laurate, 2-octyldecyl palmitate and 2-octyldodecyl myristate, purcellin oil (stearyl octanoate), isopropyl lanolate, and mixtures thereof.

The term "liquid hydrocarbon" is intended to mean a hydrocarbon composed solely of carbon and hydrogen atoms, which is liquid at 25° C., 1 atm and which is in particular of mineral or vegetable origin, preferably of vegetable origin.

As liquid hydrocarbon that may be used in the composition according to the invention, mention may be made of:

linear or branched, optionally cyclic, $C_6$-$C_{16}$ alkanes; mention may be made of hexane, undecane, dodecane, tridecane, and isoparaffins, for instance isohexadecane, isododecane and isodecane;

linear or branched hydrocarbons of mineral, animal or synthetic origin with more than 16 carbon atoms, such as volatile or non-volatile liquid paraffins, petroleum jelly, liquid petroleum jelly, polydecenes, hydrogenated polyisobutene such as the product sold under the brand name Parleam® by the company NOF Corporation, and squalane.

Preferably, when the conditioning composition according to the invention comprises one or more liquid fatty substances, it comprises them in an amount ranging from 0.1% to 30% by weight, preferably from 0.5% to 20% by weight and even better still from 1% to 10% by weight, relative to the total weight of the composition.

v) Solid Fatty Substances

The conditioning composition according to the invention may comprise, as conditioning agent, one or more solid fatty substances, in particular chosen from solid fatty alcohols, solid fatty esters, ceramides, mineral, vegetable or animal oils other than ceramides, and mixtures thereof.

The solid fatty alcohols that can be used are preferably chosen from saturated or unsaturated, linear or branched, preferably linear and saturated, (mono) alcohols comprising from 8 to 30 carbon atoms, in particular 10 to 24 carbon atoms. Mention may be made, for example, of cetyl alcohol, stearyl alcohol and a mixture thereof (cetearyl alcohol).

The solid fatty esters that may be used are preferably chosen from esters derived from $C_9$-$C_{26}$ monocarboxylic acids and from $C_9$-$C_{26}$ alcohols. Mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Esters of $C_4$-$C_{22}$ dicarboxylic or tricarboxylic acids and of $C_1$-$C_{22}$ alcohols and esters of mono-, di- or tricarboxylic acids and of di-, tri-, tetra- or pentahydroxy alcohols which are $C_2$-$C_{26}$ may also be used. Mention may be made especially of diethyl sebacate, diisopropyl sebacate, diisopropyl adipate, di-n-propyl adipate, dioctyl adipate and dioctyl maleate.

Preferentially, it is preferred to use $C_9$-$C_{26}$ alkyl palmitates, in particular myristyl, cetyl or stearyl palmitates, and $C_9$-$C_{26}$ alkyl myristates such as cetyl myristate, stearyl myristate and myristyl myristate.

The ceramides, or ceramide analogues such as glycoceramides, that can be used in the compositions according to the invention, are known per se; mention may in particular be made of ceramides of classes I, II, III and V according to the Dawning classification; they are molecules which may correspond to the formula below:

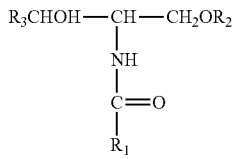

in which:
- $R_1$ denotes a linear or branched, saturated or unsaturated alkyl group, derived from $C_{14}$-$C_{30}$ fatty acids, it being possible for this group to be substituted with a hydroxyl group in the alpha-position, or a hydroxyl group in the omega-position esterified with a saturated or unsaturated $C_{16}$-$C_{30}$ fatty acid;
- $R_2$ denotes a hydrogen atom or a (glycosyl)n group, a (galactosyl)m group or a sulfogalactosyl group, in which n is an integer ranging from 1 to 4 and m is an integer ranging from 1 to 8;
- $R_3$ denotes a $C_{15}$-$C_{26}$ hydrocarbon-based group, saturated or unsaturated in the alpha-position, it being possible for this group to be substituted with one or more $C_1$-$C_{14}$ alkyl groups;

it being understood that, in the case of natural ceramides or glycoceramides, $R_3$ may also denote a $C_{15}$-$C_{26}$ alpha-hydroxyalkyl group, the hydroxyl group being optionally esterified with a $C_{16}$-$C_{30}$ alpha-hydroxy acid.

The ceramides more particularly preferred are the compounds for which $R_1$ denotes a saturated or unsaturated alkyl derived from $C_{16}$-$C_{22}$ fatty acids; $R_2$ denotes a hydrogen atom and $R_3$ denotes a linear, saturated $C_{15}$ group.

Preferentially, ceramides are used for which $R_1$ denotes a saturated or unsaturated alkyl group derived from $C_{14}$-$C_{30}$ fatty acids; $R_2$ denotes a galactosyl or sulfogalactosyl group; and $R_3$ denotes a —CH=CH—$(CH_2)_{12}$—$CH_3$ group.

Use may also be made of the compounds for which $R_1$ denotes a saturated or unsaturated alkyl radical derived from $C_{12}$-$C_{22}$ fatty acids; $R_2$ denotes a galactosyl or sulfogalactosyl radical and $R_3$ denotes a saturated or unsaturated $C_{12}$-$C_{22}$ hydrocarbon-based radical and preferably a —CH=CH—$(CH_2)_{12}$—$CH_3$ group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4 triol and in particular N-stearoylphytosphingosine; 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof.

For the purposes of the present invention, a wax is a lipophilic compound, which is solid at ambient temperature (25° C.), with a reversible solid/liquid change of state, having a melting point greater than about 40° C., which may be up to 200° C., and having in the solid state anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to ambient temperature, recrystallization of the wax in the oils of the mixture, which can be detected microscopically and macroscopically (opalescence), is obtained.

As waxes other than the ceramides above, that can be used in the present invention, mention may be made of waxes of animal origin, such as beeswaxes or modified beeswaxes (*Cera bellina*), spermaceti, lanolin wax and lanolin derivatives, vegetable waxes such as carnauba wax, candelilla wax, asparta wax, ouricury wax, Japan wax, cocoa butter or cork-fibre or sugarcane waxes, olive-tree wax, rice wax, hydrogenated jojoba wax, absolute waxes of flowers; mineral waxes, for example paraffin wax, petroleum jelly wax, lignite wax, microcrystalline waxes, ozokerites, and mixtures thereof.

Preferably, when the conditioning composition according to the invention comprises one or more solid fatty substances, it comprises them in an amount ranging from 0.1% to 20% by weight, preferably from 0.5% to 15% by weight and even better still from 1% to 12% by weight, relative to the total weight of the composition.

Preferably, the conditioning composition comprises at least one conditioning agent chosen from cationic surfactants and cationic polymers; even better still, it comprises at least one cationic surfactant.

Preferably, the conditioning agent(s) is (are) present in the conditioning composition in an amount ranging from 0.01% to 30% by weight, in particular from 0.1% to 20% by weight, even better still from 0.5% to 15% by weight, or even from 1% to 12% by weight, relative to the weight of said composition.

Application:

A subject of the present invention is therefore a process for the cosmetic treatment of keratin materials, in particular the hair, comprising the application to said keratin materials, sequentially or simultaneously:
- of a solid anhydrous cosmetic composition as described above, and
- of a conditioning composition comprising one or more conditioning agents, as described above.

In a first embodiment, the application of the solid anhydrous composition and of the conditioning composition can be sequential.

In particular, according to a first variant, it is possible, in a first step, to deposit the conditioning composition on the keratin materials, which are optionally pre-wetted, and then, in a second step, for example after a time of from 10 seconds to 2 minutes, to deposit the solid anhydrous composition on the keratin materials that will have been wetted by the application of the conditioning composition; it is then possible to carry out a step of massaging the keratin materials, so that the solid anhydrous composition disintegrates or solubilizes well; the final composition obtained can then be left on, and then the final composition can be rinsed off.

Thus, preferably, the process according to the invention comprises a step of massaging the keratin materials with the final composition.

Preferably, said process optionally comprises a step of leaving said final composition on, for example for about 2 to 15 minutes.

Preferably, said process optionally comprises a step of rinsing off the final composition, for example with water, after the optional leave-on time.

According to a second variant, it is possible, in a first step, to deposit the solid anhydrous composition on the keratin materials, which are optionally pre-wetted, and then, in a second step, for example after a time of from 10 seconds to 2 minutes, to deposit the conditioning composition on the keratin materials in order to wet them and to solubilize the solid composition; it is then possible to carry out a step of massaging the keratin materials, so that the solid anhydrous composition disintegrates or solubilizes well; the final composition obtained can then be left on, and then the final composition can be rinsed off.

Thus, preferably, the process according to the invention comprises a step of massaging the keratin materials with the final composition.

Preferably, said process optionally comprises a step of leaving said final composition on, for example for about 2 to 15 minutes.

Preferably, said process optionally comprises a step of rinsing off the final composition, for example with water, after the optional leave-on time.

In a second embodiment, the application of the solid composition and of the conditioning composition can be simultaneous.

Thus, in this particular embodiment, a subject of the invention is a process for the cosmetic treatment of keratin materials, comprising:
  (i) a step of mixing
    a solid composition comprising one or more anionic and/or amphoteric surfactants, and
    a conditioning composition comprising one or more conditioning agents, so as to obtain a final cosmetic composition; and
  (ii) a step of applying said final cosmetic composition to said keratin materials.

The mixing step can be carried out in the hand at the time of use or in a container at the time of use or beforehand, or even directly on the keratin materials.

In particular, from 0.5 to 10 g of solid anhydrous composition can be mixed with 1 to 30 g of conditioning composition; in particular from 0.5 to 5 g of solid composition can be mixed with 4 to 25 g of conditioning composition.

Preferably, the keratin materials are wetted, for example with water, before application of the final composition.

After application, a step of massaging the keratin materials can then be carried out, so that the final composition is well distributed and that the solid anhydrous composition disintegrates/solubilizes well; the final composition obtained can then be left on, and then the final composition can be rinsed off.

Thus, preferably, the process according to the invention comprises a step of massaging the keratin materials with the final composition.

Preferably, said process optionally comprises a step of leaving said final composition on, for example for about 2 to 15 minutes.

Preferably, said process optionally comprises a step of rinsing off the final composition, for example with water, after the optional leave-on time.

Kit

The kit according to the invention comprises, on the one hand, the solid anhydrous cosmetic composition as defined above and, on the other hand, the conditioning composition comprising one or more conditioning agents, as defined above.

Each of these compositions can be packaged in any of the forms that can be envisaged for this type of formulation, in particular in a bottle, a pump-dispenser bottle, a heating bottle, a tube or an aerosol. The two packagings can be completely separate and group together for example in a case or a blister pack. They can also be placed side-by-side as in the case of a double tube or a double aerosol, with a double dispensing system or with a dispensing system which pre-mixes the two compositions.

Advantageously, each of the compositions is packaged separately, in particular in a bottle, a pump-dispenser bottle or a heating bottle, and the two packagings can be separate or grouped together, advantageously grouped together.

When the kit is used, the consumer can advantageously mix the compositions with one another, for example in a suitable container; preferably, the mixing is carried out in weight proportions of 1:2 to 2:1, preferably of 1:1.

After having optionally carried out a mixing step, a final cosmetic composition ready to be applied to the keratin materials, in particular to the hair, can be obtained. This final cosmetic composition advantageously has a creamy texture and appearance.

This final cosmetic composition is especially of particularly advantageous use in the hair sector, in particular for hair hygiene, cleaning, care and/or conditioning; advantageously, it is in the form of a washing and conditioning composition, in particular in the form of a conditioning shampoo.

The final cosmetic composition may therefore optionally be rinsed off after having been applied to the keratin materials, in particular the hair. It can thus optionally be rinsed off, for example with water, after an optional leave-on time. It is preferably rinsed off, after an optional leave-on time.

A subject of the invention is also a process for the cosmetic treatment of keratin materials, comprising:
  (i) a step of mixing the solid anhydrous cosmetic composition as defined above and a conditioning composition comprising one or more conditioning agents, as defined above, so as to obtain a final cosmetic composition;
  (ii) then a step of applying said final cosmetic composition to said keratin materials.

Preferably, the mixing step is carried out just before the applying step, for example less than two hours, better still less than one hour, even better still less than 15 minutes, before the applying step.

Preferably, said process optionally comprises a step of leaving said final composition on, for example for about 2 to 15 minutes.

Preferably, said process optionally comprises a step of rinsing off the final composition, for example with water, after the optional leave-on time.

Preferably, it is a process for the cosmetic treatment, in particular the care and/or the cleaning, of keratin materials, in particular the hair, the scalp, bodily skin and/or facial skin.

In particular, it may be a cosmetic process for cleaning and conditioning human keratin materials, in particular the hair.

The present invention is illustrated in greater detail in the examples that follow (AM=active material).

EXAMPLE 1

A/ A composition for cleaning the hair is prepared in the following way:

Batch Process

A Procell fluidized air bed granulator apparatus (Glatt) with an Insert GF 3 type conical chamber, having a working volume of 2.5 litres to 10 litres, is used. The spray liquid is pumped into a reservoir and then sprayed into the chamber where the powder is placed in motion by said fluidized air bed. The air is filtered above the chamber, and the dust is regularly removed from the filters in order to recycle the fine particles.

A solid phase and a liquid phase having the following composition (in g) are prepared:

|  | Amount (in g) of starting material in the solid and liquid phases before implementation of the process | | % AM in the anhydrous final composition after passing through the granulator |
| --- | --- | --- | --- |
|  | powder | liquid sprayed | |
| SODIUM LAURYL SULFATE (TEXAPON Z 95 P from Cognis) (100% AM) | 294.6 | 58.9 | 45 + 9 (total = 54%) |
| NaCl | 40 | — | 6.1% |
| PQ10 (JR400) | 32.7 | — | 5% |
| Potato starch (SODIUM CARBOXYMETHYL STARCH) at 94% AM in water, GLYCOLYS from the company Roquette | 32.7 | — | 5% |
| COCO BETAINE at 30% AM in water | — | 621.9 | 28.5% |
| Total | 400 g | 680.8 g | 61.1% + 37.5% (the remainder being residual water) |
| Supplementary addition of water | — | Qs to achieve a pumpable and sprayable viscosity (less than 500 g) | |

The starting materials which go into making up the composition of the solid phase are premixed and then 400 g of the mixture are introduced into the spray chamber.

The starting materials which go into making up the composition of the liquid phase are premixed and then the preparation is introduced into a reservoir equipped with a peristaltic pump system for feeding the spray nozzle. The active material content of the liquid phase to be prepared is directly determined by the amount of powder introduced into the granulation chamber.

The viscosity of the preparation is adjusted by adding water so as to adapt to the maximum viscosities accepted by the pumping system. Since the solvent of the liquid phase is evaporated during the granulation, the initial dilution of the liquid phase has no impact on the final composition of the product. It is, however, carried out sparingly so as not to extend the time required by the process with an excessively large amount of liquid to be sprayed. The test ends after all of the liquid phase has been sprayed.

A solid anhydrous cosmetic composition, in the form of spherically shaped particles, which can be sieved in order to extract therefrom the particles of required size, for example ranging from 630 µm to 1 mm, is finally obtained. The residual water content does not exceed 5% by weight.

Continuous Process

The composition can also be obtained with a continuous mode of preparation in order to obtain larger amounts of product, for example with an apparatus of ProCell25 type (from the company Glatt).

The solid phase is then continuously introduced into the granulation chamber using a powder-metering device, while adjusting the flow rate relative to the liquid-phase spraying flow rate so as to guarantee the final composition.

The solid phase is gradually introduced into the granulation chamber, where it is placed in motion by the fluidized air bed. The airflow rate in the chamber is approximately 700 m$^3$/h.

The liquid phase is sprayed by means of 4 nozzles placed at the bottom of the granulation chamber; the atomization pressure is approximately 2 bar; the product temperature is approximately 50° C. with an input temperature of approximately 80° C. and an output temperature of approximately 45° C.; the temperature in the fluidized air bed is adjusted to 40° C. The granules discharged from the granulation chamber pass through a double sieve system making it possible to keep only the target fraction (of size approximately 630 µm-1 mm). The granules which are not part of this target fraction pass through a mill where they are milled and are then recycled to the granulation chamber.

A solid anhydrous cosmetic composition, in the form of spherically shaped particles having a size ranging from 630 µm to 1 mm, is finally obtained. The residual water content does not exceed 5% by weight.

B/ Evaluation

The disintegration of the composition (obtained above, batch process) by friction is evaluated: 2 g of the composition prepared above are deposited on a pre-wetted malleable head, which is lightly rubbed in order to generate foam by massaging; the disintegration is evaluated after 10 friction operations. The disintegration is considered to be rapid if there are no longer any particles visible to the naked eye. In the present case, the disintegration is very rapid.

It is also noted that the anhydrous composition according to the invention makes it possible to generate an abundant creamy foam.

The composition is then rinsed off with water and any presence of residue after rinsing is evaluated. The composition according to the invention leaves no residue.

EXAMPLE 2

The anhydrous cosmetic compositions having the following final compositions were prepared in a manner similar to Example 1:

|  | Example 2 | Example 3 | Example 4 | Example 5 | Example 6 | Example 7 | Example 8 |
|---|---|---|---|---|---|---|---|
| SODIUM LAURYL SULFATE (100% AM)(TEXAPON Z 95 P) | 54 (+0) | 45 +9 | 45 (+0) | 45 (+0) | 45 (+0) | 45 (+0) | 45 (+0) |
| SODIUM LAURYL ETHER SULFATE (70% AM in water) |  |  | (0+) 9 |  |  |  |  |
| SODIUM COCOYL ISETHIONATE (88.5% AM) (JORDAPON CI PWD) |  |  |  | (0+) 9 |  |  |  |
| DISODIUM LAURYL SULFOSUCCINATE at 96% AM in water (REWOPOL SB F 12 P) |  |  |  |  | (0+) 9 |  |  |
| SODIUM LAURYL SULFOACETATE (LATHANOL LAL POWDER) |  |  |  |  |  | (0+) 9 |  |
| SODIUM LAUROYL GLUTAMATE |  |  |  |  |  |  | (0+) 9 |
| NaCl | 6.1 | 6.1 | 6.1 | 6.1 | 6.1 | 6.1 | 6.1 |
| PQ10 (JR400) | 5 | 5 | 5 | 5 | 5 | 5 | 5 |
| SODIUM CARBOXYMETHYL STARCH - POTATO STARCH at 94% AM in water (GLYCOLYS) | 5.1 | 5.1 | 5.1 | 5.1 | 5.1 | 5.1 | 5.1 |
| COCO BETAINE at 30% AM in water |  |  | 28.5 | 28.5 | 28.5 | 28.5 | 28.5 |
| COCAMIDOPROPYL BETAINE (TEGO BETAIN CK D) at 85% AM | 28.5 | 28.5 |  |  |  |  |  |
| disintegration | rapid | rapid | rapid | rapid | rapid | rapid | rapid |
| foam | firm, good staying power, creamy | firm, good staying power, creamy | firm, good staying power, creamy | firm, good staying power, creamy | firm, good staying power, creamy | firm, good staying power, creamy | firm, good staying power, creamy |

|  | Example 9 | Example 10 | Example 11 | Example 12 | Example 13 | Example 14 | Example 15 |
|---|---|---|---|---|---|---|---|
| SODIUM LAURYL SULFATE (100% AM)(TEXAPON Z 95 P) | 45 (+0) | 45 + 9 | 45 + 9 | 45 + 9 | 45 + 9 | 45 + 9 | 45 + 9 |
| SODIUM LAURYL SULFOACETATE (LATHANOL LAL POWDER) | (0+) 9 |  |  |  |  |  |  |
| NaCl | 6.1 | 6.1 | 6.1 |  |  |  |  |
| PQ10 (JR400) | 5 | 5 | 5 | 5 | 5 |  |  |
| PQ6 at 40% AM in water (MERQUAT 100) |  |  |  |  |  | 2.4 | 2.4 |
| AMODIMETHICONE at 57.5% AM (XIAMETER MEM-8299 EMULSION) |  |  |  |  |  | 5 |  |

| | | | | | | | |
|---|---|---|---|---|---|---|---|
| CETRIMONIUM CHLORIDE at 75% AM in water | (0+) 5 | | | | | | |
| SODIUM CARBOXYMETHYL STARCH - POTATO STARCH at 94% AM in water (GLYCOLYS) | 5.1 | 5.1 | 5.1 | | | | |
| Beta-CYCLODEXTRIN at 86% AM in water | | 10.5 | 19.95 | 11.2 | | 19.3 | 24.3 |
| MONTMORILLONITE CLAY (ALUMINIUM SILICATE HYDRATE) | | | | | 11.2 | | |
| COCO BETAINE at 30% AM in water | 28.5 | 18 | 8.55 | 28.5 | 18 + 28.5 | 18 | 18 |
| disintegration | rapid | rapid | rapid | rapid | rapid | rapid | rapid |
| foam | firm, good staying power, creamy | firm, good staying power, creamy | firm, good staying power, creamy | firm, good staying power, creamy | firm, good staying power, creamy | firm, good staying power, creamy | firm, good staying power, creamy |

EXAMPLE 3

A/ A solid anhydrous cosmetic composition is prepared, using a Glatt ProCell granulator, comprising finally (% by weight of active material):

| | % active material |
|---|---|
| SODIUM LAURYL SULFATE (TEXAPON Z 95 P) | 54 |
| PQ6 at 40% AM in water (MERQUAT 100) | 2.5 |
| AMODIMETHICONE at 57.5% AM (XIAMETER MEM-8299 EMULSION) | 5 |
| Beta-CYCLODEXTRIN at 86% AM in water | 20 |
| COCO BETAINE at 30% AM in water | 18 |

B/ A liquid conditioning composition in emulsion form is prepared, comprising (% by weight of active material):

| | % active material |
|---|---|
| CETYL ALCOHOL | 4.5 |
| MIXTURE OF MYRISTYL STEARATE AND MYRISTYL PALMITATE | 1 |
| MYRISTYL ALCOHOL | 0.4 |
| BEHENYLTRIMETHYLAMMONIUM CHLORIDE | 0.42 |
| CETYLTRIMETHYLAMMONIUM CHLORIDE IN AQUEOUS SOLUTION | 0.625 |
| PDMS 60 000 K | 1 |
| DYE, FRAGRANCE | qs |
| WATER | qs 100% |

1.5 g of solid anhydrous composition are poured into 6 g of liquid conditioning composition. The mixture is applied to half the head of a volunteer. 6 g of liquid composition only are applied to the other half of the head.

The formation of a very creamy foam is observed on the side of the invention, making it possible to well coat the hair with the product. There is no foam on the side of the reference formula.

The wet hair is straight and disentangles well on both sides. The dry hair is soft and light.

The invention claimed is:

1. A disintegrable foaming solid anhydrous cosmetic composition in particle form, comprising:
at least one anionic surfactant present in an amount ranging from about 30% to about 75% by weight, relative to the total weight of the composition, wherein the at least one anionic surfactant is chosen from:
$C_6$-$C_{24}$ alkyl sulfates;
$C_6$-$C_{24}$ alkyl ether sulfates;
$C_6$-$C_{24}$ alkylsulfosuccinates;
$C_6$-$C_{24}$ alkyl ether sulfosuccinates;
($C_6$-$C_{24}$) acylisethionates;
$C_6$-$C_{24}$ acylsarcosinates;
($C_6$-$C_{24}$) alkyl ether carboxylates;
polyoxyalkylenated ($C_6$-$C_{24}$)alkyl(amido) ether carboxylic acids or salts thereof;
$C_6$-$C_{24}$ acylglutamates;
$C_6$-$C_{24}$ acylglycinates; or
mixtures thereof;
at least one amphoteric surfactant present in an amount ranging from about 5% to about 50% by weight, relative to the total weight of the composition, wherein the at least one amphoteric surfactant is chosen from ($C_8$-$C_{20}$)alkylbetaines, ($C_8$-$C_{20}$)alkylamido($C_1$-$C_6$)alkylbetaines, ($C_8$-$C_{20}$)alkylamphoacetates, ($C_8$-$C_{20}$)alkylamphodiacetates, or mixtures thereof; and
at least one filler present in an amount ranging from about 10% to about 50% by weight, relative to the total weight of the composition, wherein the at least one filler comprises at least one polysaccharide.

2. The composition according to claim 1, wherein the at least one anionic surfactant is present in an amount ranging from about 40% to about 60% by weight, relative to the total weight of the composition.

3. The composition according to claim 1, wherein the at least one amphoteric surfactant is present in an amount ranging from about 10% to about 20% by weight, relative to the total weight of the composition.

4. The composition according to claim 1, further comprising at least one polymer chosen from amphoteric or cationic polymers, or mixtures thereof, wherein the at least one polymer is present in an amount ranging from about 0.01% to about 10% by weight, relative to the total weight of the composition.

5. The composition according to claim 1, further comprising at least one silicone present in an amount ranging from about 0.01% to about 15% by weight, relative to the total weight of the composition.

6. The composition according to claim 1, wherein the size of the particles, in the largest dimension thereof, ranges from about 0.01 mm to about 5 mm.

7. A method for preparing a disintegrable foaming solid anhydrous cosmetic composition in particle form comprising spraying a liquid phase comprising at least one solvent onto a solid phase comprising at least 50% by weight, relative to the total weight of the solid phase, of at least one surfactant chosen from anionic or amphoteric surfactants, or mixtures thereof, wherein the composition comprises:
at least one anionic surfactant present in an amount ranging from about 30% to about 75% by weight, relative to the total weight of the composition, wherein the at least one anionic surfactant is chosen from:
$C_6$-$C_{24}$ alkyl sulfates;
$C_6$-$C_{24}$ alkyl ether sulfates;
$C_6$-$C_{24}$ alkylsulfosuccinates;
$C_6$-$C_{24}$ alkyl ether sulfosuccinates;
($C_6$-$C_{24}$) acylisethionates;
$C_6$-$C_{24}$ acylsarcosinates;
($C_6$-$C_{24}$) alkyl ether carboxylates;
polyoxyalkylenated ($C_6$-$C_{24}$)alkyl(amido) ether carboxylic acids or salts thereof;
$C_6$-$C_{24}$ acylglutamates;
$C_6$-$C_{24}$ acylglycinates; or
mixtures thereof;
at least one amphoteric surfactant present in an amount ranging from about 5% to about 50% by weight, relative to the total weight of the composition, wherein the at least one amphoteric surfactant is chosen from ($C_8$-$C_{20}$)alkylbetaines, ($C_8$-$C_{20}$)alkylamido($C_1$-$C_6$)alkylbetaines, ($C_8$-$C_{20}$)alkylamphoacetates, ($C_8$-$C_{20}$)alkylamphodiacetates, or mixtures thereof; and
at least one filler present in an amount ranging from about 10% to about 50% by weight, relative to the total weight of the composition, wherein the at least one filler comprises at least one polysaccharide.

8. A method for treating keratin materials, comprising:
(i) applying to the keratin materials a disintegrable foaming solid anhydrous composition in particle form, the composition comprising:
at least one anionic surfactant present in an amount ranging from about 30% to about 75% by weight, relative to the total weight of the composition, wherein the at least one anionic surfactant is chosen from:
$C_6$-$C_{24}$ alkyl sulfates;
$C_6$-$C_{24}$ alkyl ether sulfates;
$C_6$-$C_{24}$ alkylsulfosuccinates;
$C_6$-$C_{24}$ alkyl ether sulfosuccinates;
($C_6$-$C_{24}$) acylisethionates;
$C_6$-$C_{24}$ acylsarcosinates;
($C_6$-$C_{24}$) alkyl ether carboxylates;
polyoxyalkylenated ($C_6$-$C_{24}$)alkyl(amido) ether carboxylic acids or salts thereof;
$C_6$-$C_{24}$ acylglutamates;
$C_6$-$C_{24}$ acylglycinates; or
mixtures thereof;
at least one amphoteric surfactant present in an amount ranging from about 5% to about 50% by weight, relative to the total weight of the composition, wherein the at least one amphoteric surfactant is chosen from ($C_8$-$C_{20}$)alkylbetaines, ($C_8$-$C_{20}$)alkylamido($C_1$-$C_6$)alkylbetaines, ($C_8$-$C_{20}$)alkylamphoacetates, ($C_8$-$C_{20}$)alkylamphodiacetates, or mixtures thereof; and
at least one filler present in an amount ranging from about 10% to about 50% by weight, relative to the total weight of the composition, wherein the at least one filler comprises at least one polysaccharide; and
(ii) optionally, rinsing the keratin materials after a desired leave-on time.

9. The method according to claim 8, further comprising applying, sequentially or simultaneously to the application of the solid anhydrous composition, a conditioning composition comprising at least one conditioning agent chosen from cationic surfactants; cationic and/or amphoteric polymers; silicones; liquid fatty substances; solid fatty substances; or mixtures thereof.

10. The method according to claim 9, wherein the conditioning composition further comprises water in an amount of at least about 40% by weight, relative to the total weight of the conditioning composition.

11. The method according to claim 9, wherein the at least one conditioning agent is chosen from cationic surfactants, cationic polymers, or mixtures thereof.

12. The method according to claim 9, wherein the conditioning agent is present in an amount ranging from about 0.01% to about 30% by weight, relative to the weight of the conditioning composition.

13. The method according to claim 9, comprising:
(i) mixing the solid anhydrous cosmetic composition and the conditioning composition to obtain a final cosmetic composition; and
(ii) applying the final cosmetic composition to the keratin materials.

14. A kit for dyeing keratin materials, the kit comprising:
(i) a disintegrable foaming solid anhydrous cosmetic composition in particle form comprising:
at least one anionic surfactant present in an amount ranging from about 30% to about 75% by weight, relative to the total weight of the composition, wherein the at least one anionic surfactant is chosen from:
$C_6$-$C_{24}$ alkyl sulfates;
$C_6$-$C_{24}$ alkyl ether sulfates;
$C_6$-$C_{24}$ alkylsulfosuccinates;
$C_6$-$C_{24}$ alkyl ether sulfosuccinates;
($C_6$-$C_{24}$) acylisethionates;
$C_6$-$C_{24}$ acylsarcosinates;
($C_6$-$C_{24}$) alkyl ether carboxylates;
polyoxyalkylenated ($C_6$-$C_{24}$)alkyl(amido) ether carboxylic acids or salts thereof;
$C_6$-$C_{24}$ acylglutamates;
$C_6$-$C_{24}$ acylglycinates; or
mixtures thereof;
at least one amphoteric surfactant present in an amount ranging from about 5% to about 50% by weight, relative to the total weight of the composition, wherein the at least one amphoteric surfactant is chosen from ($C_8$-$C_{20}$)alkylbetaines, ($C_8$-$C_{20}$)alkylamido($C_1$-$C_6$)alkylbetaines, ($C_8$-$C_{20}$)alkylamphoacetates, ($C_8$-$C_{20}$)alkylamphodiacetates, or mixtures thereof; and
at least one filler present in an amount ranging from about 10% to about 50% relative to the total weight of the composition, wherein the at least one filler comprises at least one polysaccharide; and
(ii) a conditioning composition comprising at least one conditioning agents.

15. The composition according to claim 1 wherein the at least one filler is chosen from cyclodextrins, starches, alginates, gellans, guar gums, celluloses, wood flours, or mixtures thereof.

* * * * *